(12) United States Patent
Bonewald et al.

(10) Patent No.: US 6,358,737 B1
(45) Date of Patent: Mar. 19, 2002

(54) OSTEOCYTE CELL LINES

(75) Inventors: Lynda F Bonewald, San Antonio, TX (US); Yoichi Kato, Fuji (JP)

(73) Assignee: Board of Regents, The University of Texas System, TX (US)

( * ) Notice: Subject to any disclaimer, the term of this patent is extended or adjusted under 35 U.S.C. 154(b) by 0 days.

(21) Appl. No.: 09/152,147

(22) Filed: Sep. 11, 1998

Related U.S. Application Data

(63) Continuation-in-part of application No. 08/904,074, filed on Jul. 31, 1997, now abandoned
(60) Provisional application No. 60/058,685, filed on Sep. 12, 1997, and provisional application No. 60/022,843, filed on Jul. 31, 1996.

(51) Int. Cl.[7] .............................. C12N 5/06; C12N 5/00; A01N 63/00; A01K 67/00; A01K 67/027
(52) U.S. Cl. .................... 435/354; 435/325; 424/93.21; 800/4; 800/13; 800/18
(58) Field of Search .............................. 800/13, 14, 18, 800/4, 21; 435/325, 354; 424/93.1, 93.21

(56) References Cited

U.S. PATENT DOCUMENTS

| | | | | |
|---|---|---|---|---|
| 5,266,464 A | * | 11/1993 | Housey | 435/29 |
| 5,443,954 A | * | 8/1995 | Reddel et al. | 435/7.21 |
| 5,665,543 A | * | 9/1997 | Foulkes et al. | 435/5 |

OTHER PUBLICATIONS

Chen et al., Molecular and Cellular Differentiation, vol. 3, (3), pp. 193–212, 1995.*
Palmiter et al., Science, vol. 222, pp. 809–814, Nov. 1983.*
Pursel et al., J. Reprod. Fert., Suppl. 40: 235–245, 1990.*
Mikuni–Takagaki et al., Journal of Bone and Mineral Research, vol. 10 (2), pp. 231–242, 1995.*
Kato et al., Journal of Bone and Mineral Research, vol. 11, Supp. 1, p. T356, Aug. 1996.*
Louis–Marie Houdebine, Journal of Biotechnology, Vil. 34, pp. 269–287, 1994.*
Kappel et al., Current Opinion in Biotechnology, 3: 548–553, 1992.*
E. Brown et al.: In Vitro Characteristics of an Osteocyte–Like Cell Line from a Human Osteosarcoma, *Journal of Bone and Mineral Research,* 10(supp.1):S229 (S314), 1995, and presented at the meeting of American Society for Bone and Mineral Research.

* cited by examiner

*Primary Examiner*—Deborah J. R. Clark
*Assistant Examiner*—Shin-Lin Chen
(74) *Attorney, Agent, or Firm*—Pennie & Edmonds LLP

(57) ABSTRACT

The present invention relates to a method of producing osteocyte cell line in various stages of differentiation. Such cell line remains stable after more than 20 passages. The osteocyte has a stellate shape with dendritic processes and expresses high level of osteocalcin. More specifically, it provides a method of production for cultured osteocytes of various differentiation stages. Furthermore, it relates to osteocyte cell line, and more specifically cultured osteocyte. The invention also relates to a method for the production of monoclonal antibodies using such cultured osteocytes and further relates to hybridomas and monoclonal antibodies which recognize an osteocyte-specific antigen. Finally, the invention relates to a method of screening for modification factors and binding factors for osteocytes.

33 Claims, 33 Drawing Sheets

PICTURE OF CLONES DERIVED FROM FRACTION 10
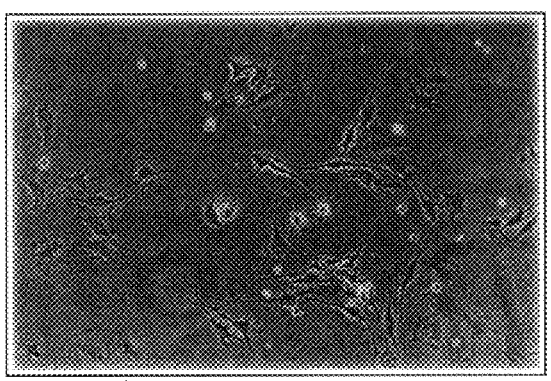
MLO-A5
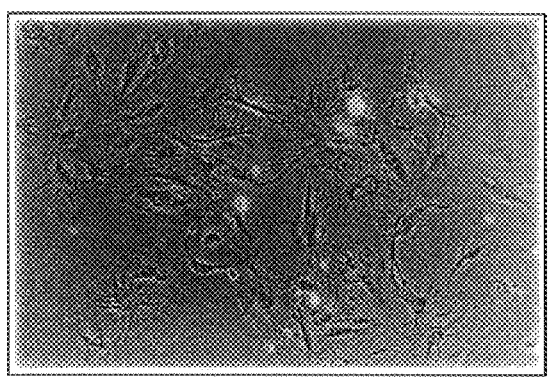
MLO-C2
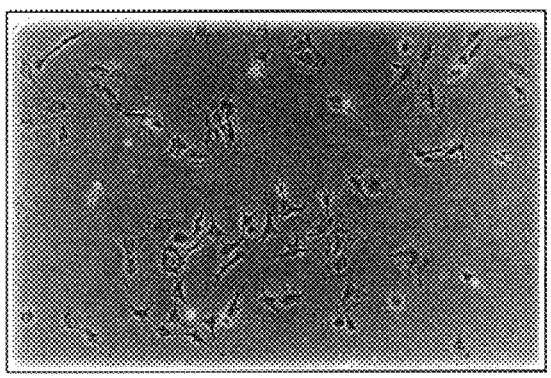
MLO-D1
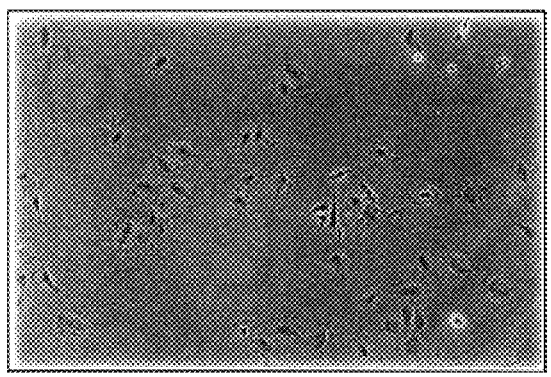
MLO-D6
*Fig. 2*

PICTURE OF THE MLO-Y CELLS OR CULTURED OSTEOCYTE FROM FRACTION 3-5

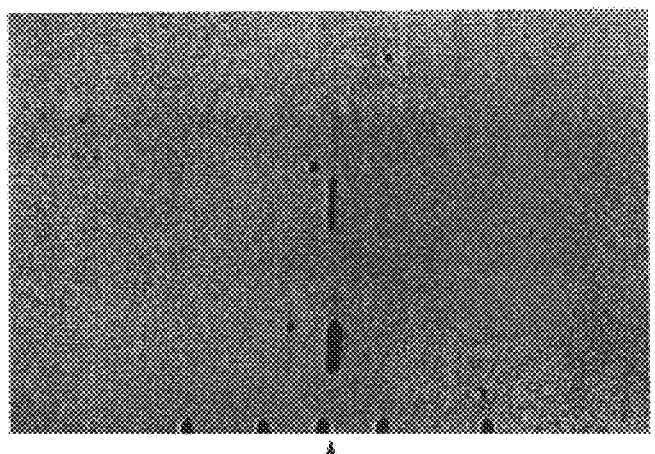
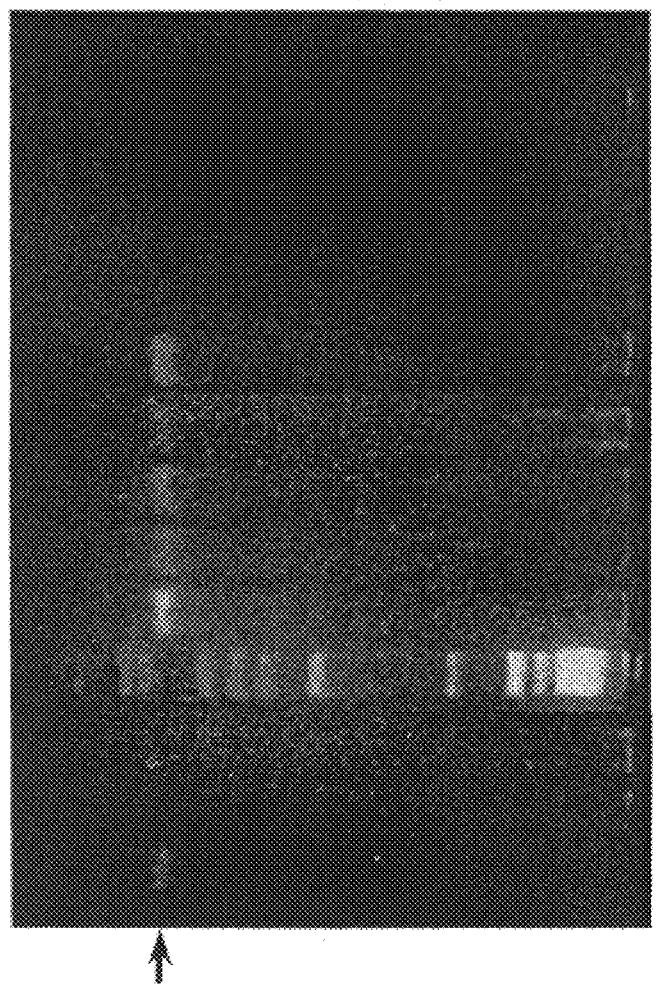
Fig. 8

CHARACTERISTICS OF MLO-A~F CELL LINES CLONES FROM FRACTION 10
| CELL LINE | D1 | D3 | D6 | C2 | A5 | F1 |
|---|---|---|---|---|---|---|
| MORPHOLOGY |  | 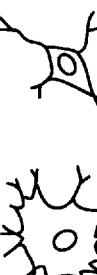 |  |  |  |  |
| ALKALIN PHOSPHATASE μ mol / mg protein / min. | 2-4 | 8-10 | 1-2 | 5-13 | 6-8 | 4-8 |
| TIME COURSE | ↑ | ↑ | ↗ | ↗ | ↑ | ↗ |
| MINERALIZATION | + | ++ | − | ++ | ++ | − |
| T-ANTIGEN mRNA | + | + | + | + | + | + |
| OSTEOCALCIN mRNA | + | + | + | + | + | + |
| ESTROGEN RECEPTOR mRNA | − | − | − | + | + | + |
*Fig. 11*

| CELL LINE | MLO-A-D | MLO-Y | MLO-Y4 | MLO-Y2 | Prim. OBl | OCT-1 | MC3T3-E1 | 2T32T9 | ST-2 |
|---|---|---|---|---|---|---|---|---|---|
| MORPHOLOGY | | | | | | | | | |
| T-ANTIGEN (WESTERN) | + | + | + | + | — | + | — | + | — |
| ALKALIN PHOSPHATASE (EA) | → OR ↘ | LOW | LOW | LOW | ↗ | ↗ | ↗ | ND | LOW |
| CONNEXIN 43 (ICC) (WESTERN) | ± / ± | ++ / ++ | +++ / +++ | ND / ND | ND / — | ± / — | ± / — | + / ND | + / ND |
| OSTEOCALCIN (RIA) | +++ | ++ | ++ | +++ | — | ± | ± | ± | — |
| OSTEOPONTIN (RT-PCR) | + | + | + | + | + | + | + | ND | ND |
| CD44 (RT-PCR) | + | + | + | ND | + | + | + | + | + |
| ESTROGEN R (RT-PCR) | −/+ | ND | + | ND | ND | + | + | + | + |
| TYPE 1 COLLAGEN (RT-PCR) | + | ± | — | ND | + | + | + | ND | ND |
| OSF-2 (RT-PCR) | + | — | — | — | + | + | + | + | (—) |

*Fig. 12*

ALKALINE PHOSPHATASE STAINING    PHASE CONTRAST PICTURE

| CELL LINE | MLO-Y4 | Prim. OBl | OCT-1 | MC3T3-E1 |
|---|---|---|---|---|
| MORPHOLOGY | | | | |
| T-ANTIGEN (WESTERN) | + | − | + | − |
| ALKALIN PHOSPHATASE (EA) | LOW | ↗ | → | ↗ |
| CONNEXIN 43 (WESTERN) | HIGH | − | − | − |
| OSTEOCALCIN (RIA) | HIGH | LOW | LOW | LOW |
| OSTEOPONTIN (RT-PCR) | + | + | + | + |
| CD44 (RT-PCR) | + | + | + | + |
| TYPE 1 COLLEGEN (RT-PCR) | LOW | + | + | + |
| OSF-2 (RT-PCR) | − | + | + | + |

*Fig. 21*

SURFACE ANTIGEN CLONE
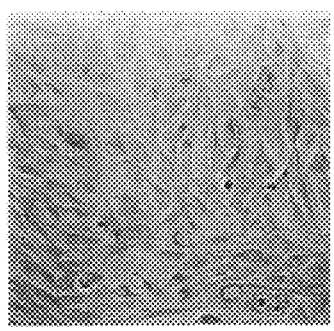
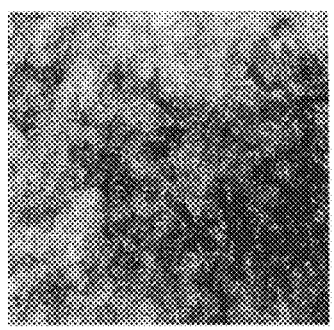
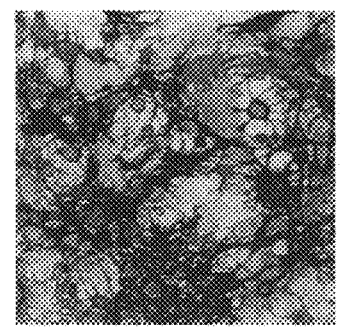
MC3T3-E1　　　　　　　OCT-1　　　　　　　MLO-Y4
*Fig. 30*

OSTEOCYTE CELL LINES

1. CROSS-REFERENCE TO RELATED APPLICATIONS

This is a non-provisional application based on provisional application serial Nos. 60/022,843 and 60/058,685, filed Jul. 31, 1996 and Sep. 12, 1997, respectively, and is a continuation-in-part of Ser. No. 08/904,074 filed Jul. 31, 1997, now abandoned.

2. BACKGROUND OF THE INVENTION

2.1 Technical Field

The present invention relates to a method of producing osteocyte cell lines in various stages of differentiation. Such cell lines remain stable after more than 20 passages. The osteocyte has a stellate shape with dendritic processes and expresses high level of osteocalcin. More specifically, it provides a method of production for cultured osteocytes of various differentiation stages. Furthermore, it relates to osteocyte cell line, and more specifically cultured osteocyte. The invention also relates to a method for the production of monoclonal antibodies using such cultured osteocytes and further relates to hybridomas and monoclonal antibodies which recognize an osteocyte-specific antigen. Finally the invention relates to a method of screening for modification factors and binding factors for osteocytes.

2.2 Description of Related Art

Bone loss can occur under conditions of disuse or with certain diseases of bone. Examples of bone loss due to disuse include that associated with immobilization and zero gravity. Bone loss can also occur due to estrogen deficiency due to menopause or ovariectomy and also occurs naturally with the aging process.

Osteocytes are the most abundant of the bone cells (approximately 25,000 per $mm^3$ bone or ten times as many osteocytes as osteoblasts) and are found within the mineralized bone matrix (Parfitt, 1977). Because they are buried in the mineralized matrix, they are relatively inaccessible and have been difficult to study in culture in homogeneous populations. It has been suggested that the osteocyte is the most mature or most terminally differentiated form of the osteoblast. However, the properties and functions of osteocytes are poorly understood.

During bone formation, some osteoblasts (osteocyte precursors) are trapped in the forming osteoid tissue while the bone formation front moves on. The trapped or encapsulated cell produces long, slender dendrite-like processes. These processes maintain contact with other osteocytes and with osteoblasts and lining cells on the bone surface (for review, see Aarden et al., 1994). Osteocytes enclosed within osteons appear to be stellate in shape and isolated osteocytes can retain this stellate shape in culture. The formation of cytoplasmic processes by the maturing osteocyte are asynchronous and asymmetrical (Palumbo et al., 1990). The cells produce dendritic processes on the mineralization side before producing processes on the vascular side. Thus the morphology of an osteocyte can range from the stellate or 'star-like' shape to that with extensive cytoplasmic, slender processes longer than the main body of the cell. Osteocytes express a dendritic phenotype both in vivo and in vitro. It has been shown previously that osteocytes express large amounts of osteocalcin.

In addition to their distinctive morphology, osteocytes are now characterized by expression of surface antigens and other markers. Osteocytes strongly express CD44, a transmembrane glycoprotein with adhesion functions (Hughes et al., 1994), and insulin-like growth factor 1 (Lean et al., 1995). Fifty percent of osteocytes in situ express estrogen receptor (Braidman et al., 1995), and avian osteocytes appear to express specific antigens detected by a monoclonal antibody not expressed on avian osteoblasts (Nijweide & Mulder, 1986). It is generally accepted that osteocytes are low expressors of alkaline phosphatase and recently it has been shown that osteocytes produce greater amounts of casein kinase activity compared with osteoblasts (Mikuni-Takagaki et al., 1995). It is very likely that mammalian osteocytes produce markers distinctly different from those of osteoblasts.

Arden and co-workers (1994) have stated that for the osteocyte to survive, the cell must maintain an unmineralized area around the body of the cell and around the cell processes. This is necessary in order to allow the diffusion of nutrients and waste products to and from the cell. Mikuni-Takagaki and co-workers (1995) described the extracellular accumulation of a large amount of osteocalcin around isolated osteocytes. Osteocalcin has been described in the endoplasmic reticulum and Golgi cisternae in osteocytes (Ohta et al., 1989; Boivin et al., 1990). Recently, Ducy and co-workers (1996) have demonstrated that mice which lack the functional gene for osteocalcin have increased cortical and trabecular bone which lead them to postulate that osteocalcin is an inhibitor or negative regulator of mineralization. The osteocyte may produce large amounts of osteocalcin to prevent the mineral from closing off the cell body and processes.

It has been hypothesized that osteocytes respond to loading pressures on bone by signaling osteoblasts to produce new bone (for review, see Burger et al., 1993). Recently it has been shown that loaded bone contains fewer apoptotic osteocytes (Noble et al., 1997) and that osteocyte cell death is increased during estrogen withdrawal (Tomkinson et al., 1996) and during treatment with excess glucocorticoid (Weinstein et al., 1997) suggesting that bone loss or bone necrosis is due to osteocyte death which prevents normal bone remodeling or normal bone repair. If osteocytes are the cell responsible for sensing mechanical stress and for signaling osteoblasts to produce new bone, then understanding their functions could lead to new therapies to prevent or restore bone loss due to immobilization or other processes.

The study of osteocytes has utilized immunohistochemistry techniques and the isolation of primary cells. However, primary cells can only be obtained in relatively low numbers and in heterogeneous populations. An osteocyte cell line would prove useful to study the properties of osteocytes through the use of molecular and functional techniques which require relatively large numbers of homogeneous cells.

We postulated that since osteocytes are large producers of osteocalcin, that bone cells derived from transgenic mice overexpressing the T-antigen driven by the osteocalcin promoter which would serve to target large T-antigen to osteoblasts and osteocytes, and thereby be a source of immortalized cells of these types. We chose to use cellular morphology as the initial criteria for cloning cell lines with osteocytes characteristics from isolates from these mice (Chen et al., 1995). Once clonal cell lines were established, they were characterized as far as the osteocyte/osteoblast phenotypes were concerned.

With regard to the generation of monoclonal antibodies specific for osteocytes, Nijweide and co-workers reported a monoclonal antibody which recognizes avian osteocytes but not mammalian osteocytes (Nijweide and Mulder, 1986). This monoclonal antibody was generated by injecting mice with osteoblast-like cells derived from digestions of chick embryol calvaria which had been cultured 6 days before injection. This monoclonal antibody specifically reacts with the cell surface of osteocytes and not with any specific band by western blotting of chick osteocyte lysate. The specificity of this monoclonal antibody has been confirmed by Bruder and Caplan (1989) and this antibody has been used as a tool to purify osteocytes (Vanderplas et al., 1994) and investigate osteocyte function (Tanaka et al., 1995).

Another monoclonal antibody which recognizes the osteoblast to osteocyte transition has been generated. This antibody recognizes a cell surface antigen called E11 in rats which is homologous to the OTS-8/ap38 molecule in mice (Wetterwald et al., 1996). This monoclonal antibody was generated by injecting mice with the rat osteoblastic cell line IRC 10/30-myc3. The E11 transcript was detected in bone, lung, brain, and skin. This antigen appears to be expressed during the transition stage from the osteoblast to the osteocyte phenotype. Over-expression of E11 in ROS 17/2.8 cells caused these cells to form long cytoplasmic extensions (Sprague et al., 1996). Therefore this antigen appears to be an osteocyte differentiation agent.

We were successful in generating monoclonal antibodies which are specific for mammalian osteocytes, by immunizing a rat with the cultured osteocytes originated from the osteocyte cell lines of the current invention.

These cell lines and monoclonal antibodies should prove to be useful tools to examine the functions of osteocytes as a whole as well as to characterize osteocyte specific antigens and their roles in osteocyte function.

References related to the invention as cited above and also references hereinafter are listed herein below:
1. Aarden E M, Burger E H, Nijweide P J. Function of osteocytes in bone. J Cell Biochem 55:287–299, 1994.
2. Bharagava U, Bar-Lev, Bellows C G, Aubin J E. Ultrastructural analysis of bone nodules formed in vitro by isolated fetal rat calvarial cells. Bone 9:155–163, 1988.
3. Boivin G, Morel, G, Lian J B, Anthoine-Terrier C, Dubois P M, Meunier P J. Localization of endogeneous osteocalcin in neonatal rat bone and its absence in articular cartilage: Effect of warfarin treatment. Virchows Archiv A Pathol Anat Histopathol 417:505–512, 1990.
4. Bodine P V N, Vernon S K, Komm B S Establishment and hormonal regulation of a conditionally transformed preosteocytic cell line from adult human bone. Endocrinology 137:4592–4604, 1996.
5. Bonewald L F, Wakefield L, Oreffo R O C, Escobedo A, Twardzik D R, Mundy G R. Latent forms of transforming growth factor-β (TGF-β) derived from bone cultures: Identification of a naturally occurring 100-kDa complex with similarity to recombinant latent TGF-β. Molecular Endocrinology 5:741–751, 1991.
6. Bonewald L F, Kester M B, Schwartz Z, Swain L D, Khare A, Johnson T L, Leach K J, Boyan B D. Effects of combining transforming growth factor beta (TGF β) and 1,25 dihydroxyvitamin $D_3$ on differentiation of a human osteosarcoma (MG-63). J Biol Chem 267:8943–8949, 1992.
7. Boyan B D, Schwartz Z, Bonewald L F, Swain L D. Localization of 1,25(OH)2D3 responsive alkaline phosphatase in osteoblast-like cells (ROS 17/2.8, MG-63 and MC3T3) and growth cartilage cells in culture. J Biol Chem 264:117879–11886, 1989.
8. Braidman I P, Davenport L K, Carter D H, Selby P L, Mawer E B, Freemont A J. Preliminary in situ identification of estrogen target cells in bone. J Bone Miner Res 10:74–80, 1995.
9. Bruder S P, Caplan A L. First bone formation and the dissection of an osteogenic lineage in the embryonic chick tibia is revealed by monoclonal antibodies against osteoblasts. Bone 10:359–375, 1989.
10. Bruder S P, Caplan A L. Terminal differentiation of osteogenic cells in the embryonic chick tibia is revealed by a monoclonal antibody against osteocytes. Bone 11:189–198, 1990.
11. Burger E H, Veldhuijzen J P. Influence of mechanical factors on bone formation resorption, growth in vitro. In: Hall B K (ed), Bone. CRC Press, Inc., Boca Raton, Fla., 7:37–56, 1993.
12. Chen D, Chen H, Fend J Q, Windle J J, Koop B A, Harris M A, Bonewald L F, Boyce B F, Wozney J M, Mundy G R, Harris Se. Osteoblastic cell lines derived from a transgenic mouse containing the osteocalcin promoter driving SV40 T-antigen. Molec. Cell Diff. 3:193–212, 1995.
13. Chiba H, Sawada N, Oyamada M, Kojima T, Iba K, Ishii S, Mori M. Hormonal regulation of connexin 43 expression and gap junctional communication in human osteoblastic cells. Cell Struc Funct 19:173–177, 1994.
14. Chiba H, Sawada N, Oyamada M, Kojima T, Nomura S, Ishii S, Mori M. Relationship between the expression of the gap junction protein and osteoblast phenotype in a human osteoblastic cell line during cell proliferation. Cell Struc Funct 18:419–426, 1993.
15. Civitelli R, Beyer E C, Warlow P M, Robertson A J, Geist S T, Steinberg T H Connexin 43 mediates direct intercellular communication in human osteoblastic cell networks. J Clin Invest 91:1888–1896, 1993.
16. Ducy P, Desbois C, Boyce B, Pinero G, Story B, Dunstan C, Smith E, Bonadio J, Goldstein S, Gundberg C, Bradley A, Karsenty G. Increased bone formation in osteocalcin-deficient mice. Nature 382:448–452, 1996.
17. Edelson E Conduits for cell/cell communication. MOSAIC 21:48–56, 1990.
18. Efrat S, Linde S, Kofod H, Sprector D, Delannoy M, Gant S, Hanahan D, Kaekkeskov S. Beta-cell lines derived from transgenic mice expressing a hybrid insulin gene-oncogene. Proc Natl Acad Sci USA 85:9037–9041, 1988.
19. Ghosh-Choudhury N, Windle J J, Koop B A, Harris M A, Guerrero D L, Wozney J M, Mundy G R, Harris S E. Immortalized murine osteoblasts derived from BMP-2 T-antigen expressing transgenic mice. Endocrinology 137:3331–330, 1996.
20. Harris S E, Sabatini M, Harris M A, Feng J, Mundy G R. Expression of bone morphogenetic protein messenger RNA in prolonged cultures of fetal rat calvarial cells. J Bone Miner Res 9:389–394, 1994.
21. Hassan H J, Aubin J E CD44 expression in fetal rat bone: in vivo and in vitro analysis. Exp Cell Res 223:467–477, 1996.
22. Hirakawa K, Hirota S, Ikeda T, Yamaguchi A, Takemura T, Nagoshi J, Yoshiki S, Suda T, Kimura Y, Nomura S. Localization of the mRNA for bone matrix proteins during fracture healing as determined by in situ hybridization. J Bone Miner Res 9:1551–1557, 1994.
23. Hughes D E, Salter D M, Simpson R. CD44 expression in human bone: A novel maker of osteolytic differentiation. J Bone Miner Res 9:39–44, 1994.
24. Ikeda T, Nagai Y, Yamaguchi A, Yokose S, Yoshiki S. Age-related reduction in bone matrix protein mRNA expression in rat bone tissues: application of histomorphometry to in situ hybridization. Bone 16:17–23, 1995.

25. Kato Y, Windle J J, Koop B A, Mundy G R, Bonewald L F. Establishment of an osteocyte-like cell line, MLO-Y4. J. Bone. Min. Res. (in press).
26. Klein-Nulend J, Van Der Plas A, Semeins C M, Ajubi N E, Frangos J A, Nijweide P J, Burger E H. Sensitivity of osteocytes to biomechanical stress in vitro. FASEB J 9:441–445, 1995.
27. Kodama H, Amagai Y, Sudo H, Kasai S, Yamamoto S. Establishment of a clone osteogenic cell line from newborn mouse calvaria. Jpn J Oral Biol 23:899–893, 1982.
28. Lean J M, Jagger C J, Chambers T J, Chow J W M. Increased insulin-like growth factor I mRA expression in rat osteocytes in response to mechanical stimulation. Am J Physiol 268 Endocrinol Metab 31:E318–E327, 1995.
29. Mason D J, Hillam R A, Skerry T M Constitutive in vivo mRNA expression by osteocytes of β=actin, osteocalcin, connexin 43, IGF-I, c-fs and c-jun, but not TNF-α nor tartrate-resistant acid phosphatase. J Bone Miner Res 11:350–357, 1996.
30. Mikuni-Takagaki Y, Kakai Y, Satoyoshi M, Kawano E, Suzuki Y, Kawase T, Saito S. Matrix mineralization and the differentiation of osteocyte-like cells in culture. J Bone Miner Res 10:231–242, 1995.
31. Mikuni-Takagaki Y, Suzuki Y, Kawase T, Saito S. Distinct responses of different populations of bone cells to mechanical stress. Endocrinology 137:2028–2035, 1996.
32. Nakamura H, Kenmotsu S, Sakai H, Ozawa H. Localization of CD44, the hyaluronate receptor, on the plasma membrane of osteocytes and osteoclasts in rat tibiae. Cell Tissue Res 280:225–233, 1995.
33. Nijweide P J, Mulder R J P. Identification of osteocytes in osteoblast-like cell culture using a monoclonal antibody specifically directed against osteocytes. Histochemistry 84:342–347, 1986.
34. Noble B S, Stevens H, Mosley J R, Pitsillides A A, Reeve J, Lanyon L. Bone loading changes the number and distribution of apoptotic osteocytes in cortical bone. J. Bone Min Res 12 Supl 1, Abstract #36, 1997.
35. Ohta T, Mori M, Ogawa K, Matsuyama T, Ishii S. Immunocytochemical localization of BGP in human bones in various developmental stages and pathological conditions. Virchows Arch A Pathol Anat Histopathol 415:459–466, 1989.
36. Oi V T, Herzenberg L A (1980) Immunoglobulin-producing cell lines, p. 351–372 In: B. B. Mishell and S. M. Shiigi (eds), "Selected Methods in Cellular Immunology, W.H. Freeman and Co., San Francisco, Calif.
37. Palumbo C, Palazzini S, Marotti G. Morphological study of intercellular junctions during osteocyte differentiation. Bone 11:401–406, 1990.
38. Palumbo C, Palazzini S, Zaffe D, Marotti G. Osteocyte differentiation in the tibia of newborn rabbit: An ultrastructural study of the formation of cytoplasmic processes. Acta Anat 137:350–358, 1990.
39. Parfitt A M. The cellular basis of bone turnover and bone loss. Clin Orthop Rel Res 127:236–247, 1977.
40. Pead M J, Suswillo R, Skerry T M, Vedi S. Lanyon L E Increased $^3$H uridine levels in osteocytes following a single short period of dynamic loading in vivo. Calcif Tissue Int 43:92–96, 1988.
41. Rawlinson S C, Mohan S, Baylink D J, Lanyon L E. Exogenous prostacyclin, but not prostaglandin E2, produces similar responses in both G6PD activity and RNA production as mechanical loading, and increases IGF-11 release, in adult cancellouse bone in culture. Calcif Tissue Int 53:324–329, 1993.
42. Sandberg M, Autio-Harmainen H, Vuorio E. Localization of expression of type I, III, and IV collagen, TGF-β1 and c-fos genes in developing human calvarial bone. Dev Biol 130:324–334, 1988.
43. Schirrmacher K, Schmiz I, Winterhager E, Traub O, Bremmer F, Jones D, Binbmann D. Characterization of gap junctions between osteoblast-like cells in culture. Calcif Tissue Int 51:285–290, 1992.
44. Schiller P C, Mehta P P, Roos B A, Howard G A. Hormonal regulation of intercellular communication: Parathyroid hormone increases connexin 43 expression and gap-junctional communication in osteoblastic cells. Mol Endocrinol 6:1433–1440, 1992.
45. Skerry T M, Bitensky L, Chayen J, Lanyon L E. Early strain-related changes in enzyme activity in osteocytes following bone loading in vivo. J Bone Miner Res 4:783–788, 1989.
46. Sprague L, Wetterwald A., Heinzman U, Atkinson M J. Phenotypic changes following over-expression of sense of antisense E11 cDNA in ROS 17/1.8 cells. J. Bone Min. Re. Vol. 11, Supl #151, p. S132, 1996.
47. Steinberg T H, Civitelli R, Geist S T, Robertson A J, Hick E, Veenstra R D, Wang H-Z, Warlow P M, Westphale E M, Laing, J G, Beyer E C. Connexin 43 and connexin 45 form gap junctions with different molecular permeabilities in osteoblastic cells. EMBO J 13:744–750, 1994.
48. Takahashi N, Akatsu T, Udagawa N, Sasaki T, Yamaguchi A, Moseley J M, Martin T J, Suda T. Osteoblastic cells are involved in osteoblast formation. Endocrinology 123:2600–2602, 1988.
49. Takeshita S, Kikuno R, Tezuka K, Amann E. Osteoblast-specific factor 2: cloning of a putative bone adhesion protein with homology with the insect protein fasciclin J. Biochem J 294:271–278, 1993.
50. Tanaka K, Mutsue T, Ohta M, Sato T, Tezuka K, Nijweide P J, Katoh Y, Hakeda Y, Kumegawa. Time-Lapse microcinematography of osteocytes. Miner. Electrolyte Metab; 21:189–192, 1995.
51. Tomkinson B, Reeve J, Shaw R W, Noble B S. The death of osteocytes by apoptosis in human bone is observed following oestrogen withdrawal by GnRH analogues, Abt #01 p. 1812, 1996.
52. Turner C H, Forwood M R. What role does the osteocyte network play in bone adaptation? Bone 16:283–285, 1995.
53. van der Plas A, Nijweide P J. Isolation and purification of osteocytes. J Bone Miner Res 7:389–396, 1992.
54. Vanderplas A, Aarden E M, Feijen J H M, Deboer A H, Wiltink A, Alblas M J, Deleij L, Nijweide P J. Characteristics and properties of osteocytes in culture. J. Bone Min. Res. 9:1697–1704, 1994.
55. Weinstein R S, Jilka R L, Miller F L, Parfitt A M, Manologas S C. Glucocorticoid excess causes apoptosis of osteocytes in murine cortical bone: A potential explanation for "bone necrosis". J. Bone Min. Res. 12 Supp 1 Abst #158, 1997.
56. Wetterwald A, Hofstetter W, Cecchini M G, Lanske B, Wagner C, Fleisch H, Atkinson M. Characterization and cloning of the E11 antigen, a marker expressed by rat osteoblasts and osteocytes. Bone, 18: 125–132, 1996.
57. Windle J J, Weiner R I, Mellon P L. Cell lines of the pituitary gonadotrope lineage derived by targeted oncogenesis in transgenic mice. Mol Endocrinol 4:597–603, 1990.

Establishment of an osteocyte cell line would make possible studies using molecular and functional techniques which require large numbers of cells in a homogeneous population. First, monoclonal antibodies could be developed which specifically recognize osteocytes. These antibodies could be used for immunocytochemistry and affinity purification of primary osteocytes as well as characterization of osteocyte-specific antigens and their role in osteocyte function. Secondly, these cells could be used to examine the effects of mechanical stress as potential signaling factors may be released by these cells. Molecular techniques could be used to examine regulation of messenger RNA and subtraction techniques could be utilized to determine which factors are induced by mechanical stress. Thirdly, these cells could be used to determine cell-cell communication between osteocyte-osteocyte, osteocyte-osteoblast, and even osteocyte-osteoclast. Expression of connexins and gap junction proteins could be examined. Fourthly, these cells could be used to examine the effects of unknown compounds on the functional characteristics of osteocytes to develop potential new therapies to induce new bone formation. Fifthly, these cells could be used to screen for modification factor of the osteocyte cell line by monitoring a material such as NO, NOS activity, prostaglandins, COX activity, osteocalcin, IGFs, TGF-beta, connexins, kinase activity, $Ca^{2+}$ uptake, ion channel activity and 3[H]-thymidine uptake. Lastly, these cells could be used to screen for factors that bind to the osteocyte.

We describe herein the establishment of several cell lines with the characteristics of osteocytes derived from transgenic mice which overexpress the T-antigen driven by the osteocalcin promoter. These cell lines were characterized and their properties compared with the known properties of primary osteocytes, osteoblasts, and other cells. They display various degrees of dendritic processes, are high producers of osteocalcin and osteopontin. In certain mature osteocyte cell lines, connexin 43 is expressed in high levels. Both control osteoblast cell line and the primary osteocytes cell line express CD44, therefore CD44 is not a specific marker for osteocytes. Furthermore, several osteocyte cell lines formed mineral on their cell surface. Most interestingly, one of the cell lines established, MLO-Y4 for 'murine long bone osteocyte' has properties that are very similar to primary osteocytes. Like primary osteocytes and unlike primary osteoblasts, the cell line produces large amounts of osteocalcin but low amounts of alkaline phosphatase. The cells produce extensive, complex dendritic processes, are positive for T-antigen, for osteopontin, for the neural antigen CD44, and for connexin 43, a protein found in gap junctions. This cell line also produces very small amounts of type I collagen mRNA compared with primary osteoblasts. MLO-Y4 cells lack detectable mRNA for osteoblast-specific factor 2 (OSF-2) which appears to be a positive marker for osteoblasts but may be a negative marker for osteocytes. OSF-2 is highly expressed in primary osteoblasts and MC3T3-E1 cells, but not apparently in osteocytes. The cloned dendritic cell lines may represent various stages of differentiation of the osteocyte.

We also describe herein the generation of monoclonal antibodies which specifically recognize osteocyte-specific antigens expressed at different sites and/or different stages of osteocytes.

Accordingly, it is an object of present invention to provide a method of producing osteocyte cell line in various stages of differentiation. Such osteocyte cell line remains stable after more than 20 passages. The osteocyte has a stellate shape with dendritic processes and expresses high levels of osteocalcin.

Another object is to provide a method of production for cultured osteocyte which remains stable after more than 20 passages. The osteocyte has a stellate shape with dendritic processes and expresses high levels of osteocalcin.

Another object is to provide osteocyte cell line of a differentiation stage which remains stable after more than 20 passages. The osteocyte has a stellate shape with dendritic processes and expresses high levels of osteocalcin.

Yet another object is to provide a cultured osteocyte which remains stable after more than 20 passages. The osteocyte has a stellate shape with dendritic processes and expresses high levels of osteocalcin.

Yet another object is to provide a method of producing monoclonal antibodies which specifically recognize osteocyte-specific antigens.

Yet another object is to provide monoclonal antibodies which specifically recognize osteocyte-specific antigens.

Yet another object is to provide a method of screening for modification factors of the osteocyte cell line.

Yet another object is to provide a method of screening for binding factors with the osteocyte.

These and other objects of the invention as well as a fuller understanding of the advantages thereof, can be had by reference to the following description and claims.

3. SUMMARY OF THE INVENTION

The invention provides a method of producing osteocyte cell line in various stages of differentiation. Such cell line remains stable after more than 20 passages. The osteocyte has a stellate shape with dendritic processes and expresses high levels of osteocalcin. The method comprises the steps of preparing a transgenic animal carrying an osteocalcin promoter driven T-antigen transgene. Bones are then isolated from the transgenic animal and digested with collagenase solution. The cells are then harvested into fetal and adult calf serum supplemented medium. The harvested cells are then plated and a cell line is isolated by selecting single colony.

The invention also provides a method of producing osteocyte cell line in various stages of differentiation. Such cell line remains stable after more than 20 passages. The osteocyte has a stellate shape with dendritic processes and expresses high levels of osteocalcin. The method comprises the steps of preparing a transgenic animal carrying an osteocalcin promoter driven T-antigen transgene. Bones are then isolated from the transgenic animal and digested with collagenase solution. The remaining bone pieces are then harvested and alternately treated with EDTA and collagenase. The remaining bone pieces are then minced into smaller chips. The bone chips are then cultured for a period sufficient to allow migration of cells from the bone chips. The migrated cells are then harvested and cultured with fetal and adult calf serum supplemented medium. A cell line is then isolated by selecting single colony.

The invention further provides a method of producing cultured osteocyte. The cultured osteocyte remains stable after more than 20 passages. It has a stellate shape with dendritic processes and expresses high levels of osteocalcin. The method comprises the steps of preparing a transgenic animal carrying an osteocalcin promoter driven T-antigen transgene. The bones are then isolated from the transgenic animal and digested with collagenase solution. The cells are then harvested and cultured with fetal and adult calf serum supplemented medium.

The invention yet further provides a method of producing cultured osteocytes. The cultured osteocyte remains stable after more than 20 passages. The osteocyte has a stellate shape with dendritic processes and expresses high levels of osteocalcin. The method comprises the steps of preparing a transgenic animal carrying an osteocalcin promoter driven T-antigen transgene. The bones are then isolated from the transgenic animal and digested with collagenase solution. The remaining bone pieces are then harvested and alternately treated with EDTA and collagenase. The remaining bone pieces are then minced into smaller chips. The bone chips are then cultured for a period sufficient to allow migration of cells from bone chips. The migrated cells are then harvested and cultured with fetal and adult calf serum supplemented medium.

Yet the invention further relates to a osteocyte cell line in various stages of differentiation. The osteocyte cell line remains stable after more than 20 passages. The osteocyte has a stellate shape with dendritic processes and expresses high levels of osteocalcin.

Yet the invention further relates to a cultured osteocyte. The cultured osteocyte remains stable after more than 20 passages. The osteocyte has a stellate shape with dendritic processes and expresses high levels of osteocalcin.

Yet the invention further provides a method of producing monoclonal antibodies which specifically recognize osteocyte-specific antigens. The method comprises the steps of immunizing an animal with cultured osteocytes prepared by the current invention as described above, obtaining antibody-producing cells from the immunized animal, forming hybridomas by fusing antibody-producing cells with immortalizing cells and harvesting the monoclonal antibodies produced by the hybridomas.

Yet the invention further provides monoclonal antibodies which specifically recognize osteocyte-specific antigens.

Yet the invention further provides a method of screening for modification factors of the osteocyte cell line by monitoring a material such as NO, NOS activity, prostaglandins, COX activity, osteocalcin, IGFs, TGF-beta, connexins, kinase activity, $Ca^{2+}$ uptake ion channel activity and 3[H]-thymidine uptake.

Yet the invention further provides a method of screening for factors that binds to osteocytes.

4. DESCRIPTION OF THE DRAWINGS

Referring to the drawings,

FIG. 1 is a Flow diagram depicting how the fractions 3–5 and fraction 10 were derived from the long bones of 14 day old transgenic mice which express large T-antigen driven by the osteocalcin promoter. The cell lines MLO-Y4 and Y2 were derived from cells isolated only with collagenase digestion (derived from fractions 3–5), whereas the cell lines MLO-A to F (fraction 10) had been alternately treated with collagenase and EDTA treatment.

FIG. 2 depicts clones (A5, C2, D1, D6) derived from fraction 10. Note the shapes ranging from small stellate cells to expression of slender, extended dendritic processes.

FIG. 8 shows the expression of T-antigen by western blot analysis and expression of osteocalcin by RT-PCR in cultured osteocyte:MLO-Y and compared to other cell lines.

FIG. 11 is a table listing the characteristics of cell lines MLO-A to F cloned from fraction 10.

FIG. 12 is a table listing the characteristics of the cultured osteocyte:MLO-Y and cell lines derived from the cultured osteocyte:MLO-Y as compared to the cell lines from fraction 10 and also as compared to a series of osteoblast like cells.

FIG. 14 is a time course showing the morphological appearance of the MLO-Y4 cell line from 3 hours to 7 days after seeding on collagen-coated plates. At three hours the cells are small and stellate. Note the extension and increased branching of dendritic processes over time in culture. At seven days, cell growth appears contact inhibited. A=3 hours, B=6 hours, C=24 hours, D=58 hours, E=4 days, F=7 days.

Figure 15:
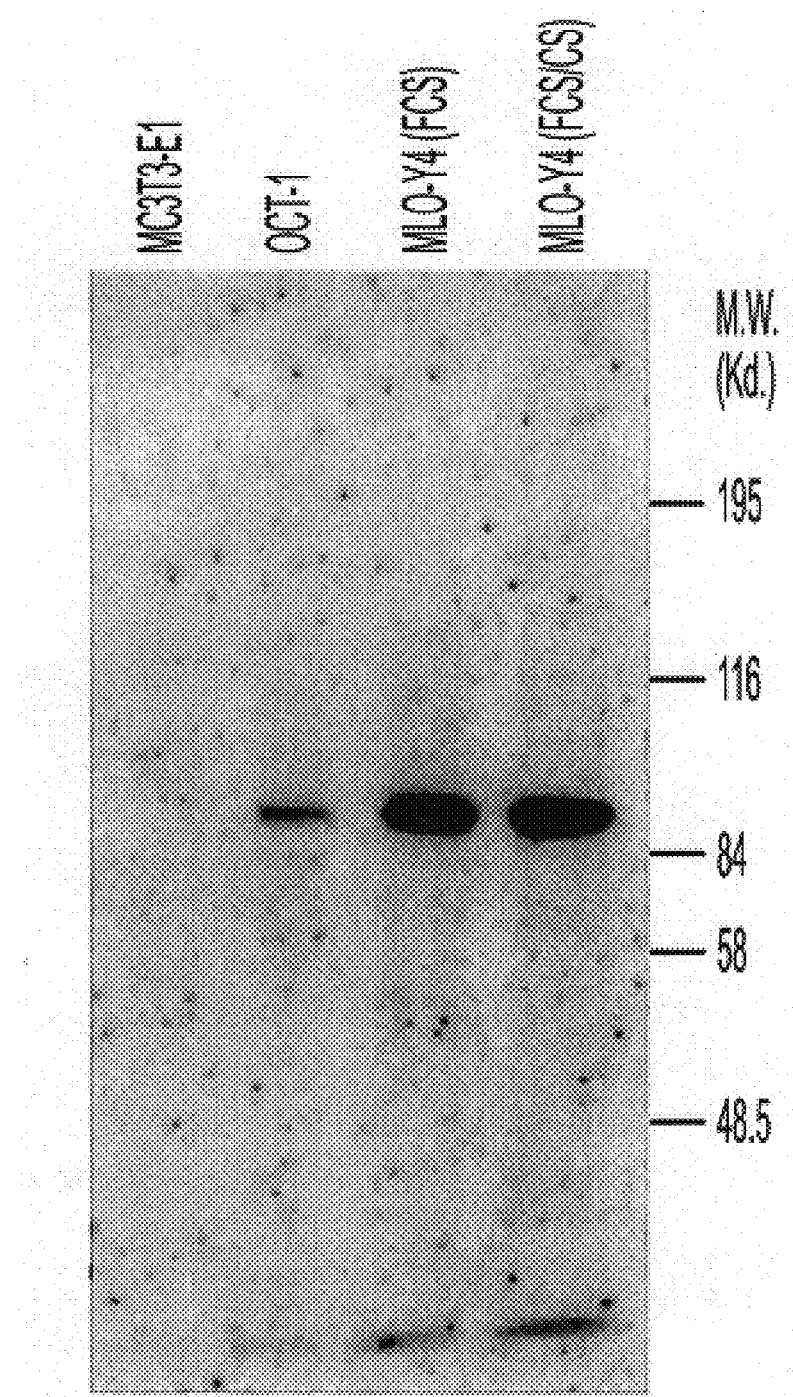

FIG. 15 is a Western blot showing expression of T-antigen by MLO-Y4 cells grown in 10% FCS or 5% FCS/5% CS and OCT-1 cells but not MC3T3-E1 cells.

FIG. 16-(A) is a growth curve of the MLO-Y4 cell line under various culture conditions (10% FCS or 5% FCS/5% CS, with or without collagen coating of surfaces) compared to the osteoblastic cell line, OCT-1. (B) shows the proliferation rate of the MLO-A to MLO-D cell lines.

FIG. 17 depicts the staining for the alkaline phosphatase enzyme (left) and phase contrast (right) of MLO-Y4 cells (A). Original magnification is 50×. Few cells are positive for alkaline phosphatase. Note the extensive cellular processes emphasized by phase contrast. Alkaline phosphatase specific activity of MLO-Y4 as compared to primary osteoblasts (Prim. OB1) and the osteoblastic cell line; OCT-1 (B). The cells were cultured for 15 days using 10% FCS containing culture conditions. The results are presented as the mean±SD, n=3. Note the continuous low expression of alkaline phosphatase in the MLO-Y4 cell line. Similar results were observed using 5% FCS/5% CS containing culture conditions (data not shown).

Figure 18A:
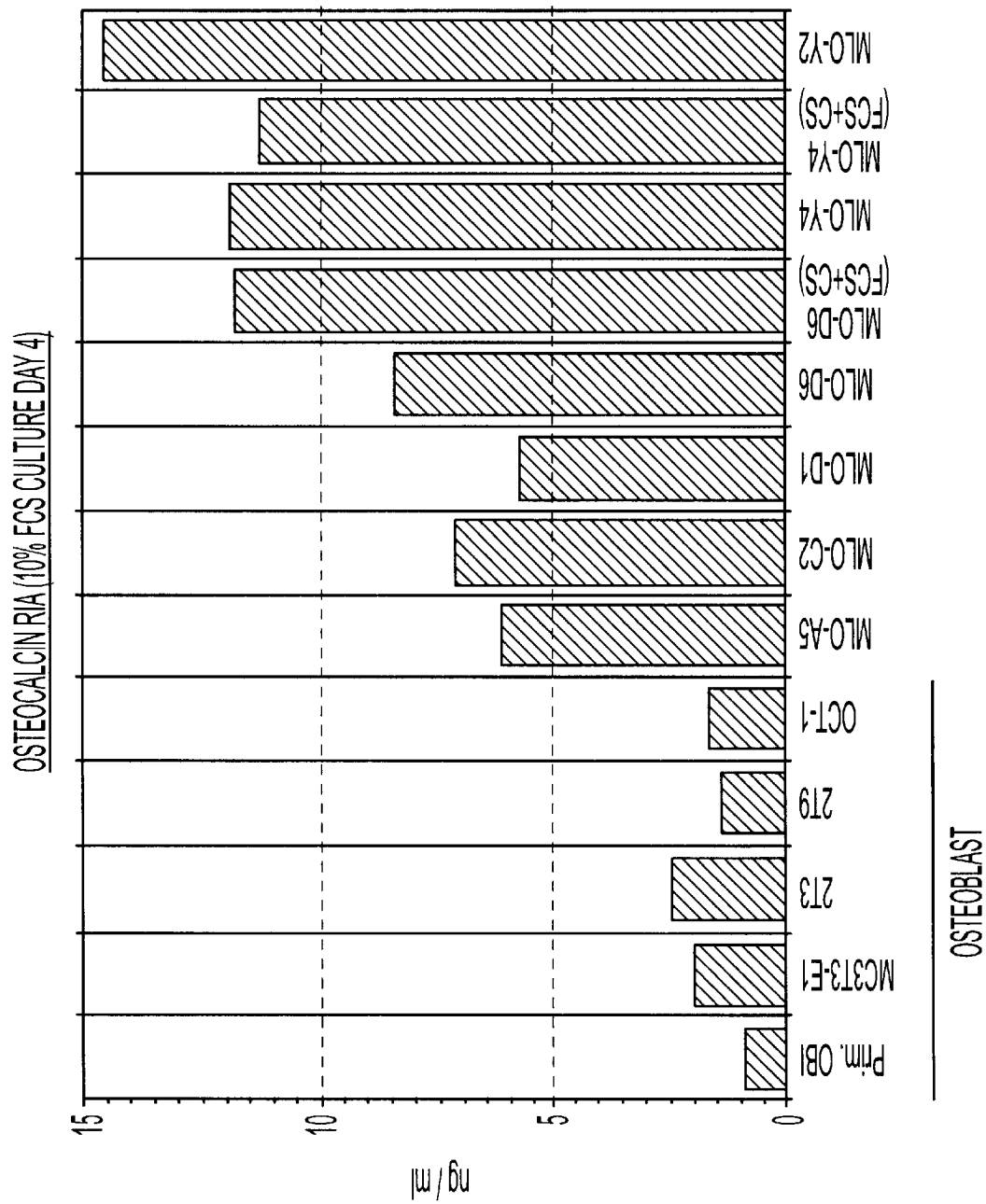
Figure 18B:
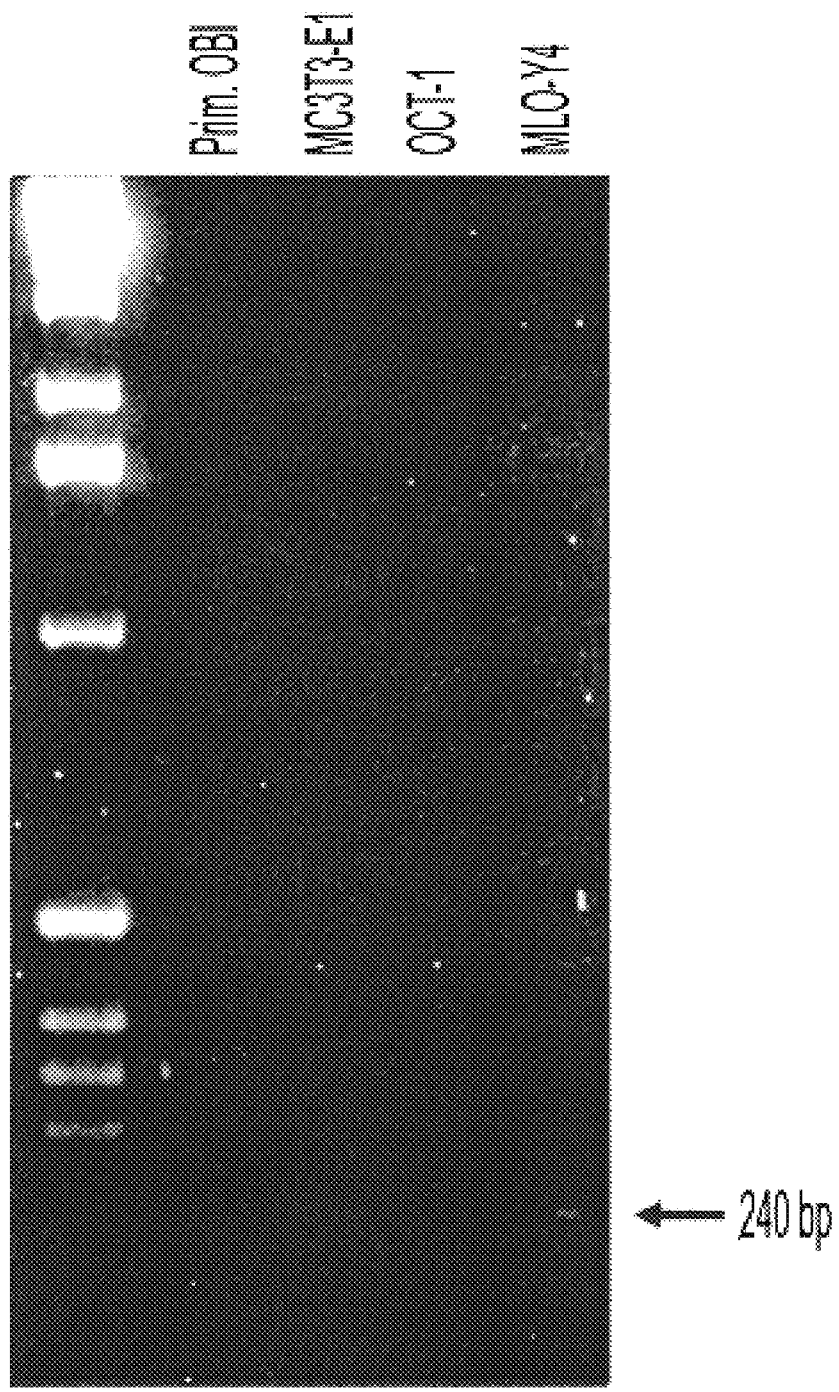

FIGS. 18A and 18B depict the osteocalcin protein and mRNA expression by MLO-Y4 cells. (A) shows the osteocalcin production in conditioned media of the MLO-Y4 clone compared to primary osteoblast cells and two osteoblast cell lines MC3T3-E1 and OCT-1 as determined by radioimmunoassay. MLO-Y4 cells produce large amounts of osteocalcin whether cultured in 10% FCS or 5% FCS/5% CS compared to primary osteoblast cells, MC3T3-E1 and OCT-1, cultured in 10% FCS (n=2). (B) shows the expression of osteocalcin MRNA in the MLO-Y4 cell line when compared to osteoblast cells as determined by RT-PCR. A band is present in the MLO-Y4 lane but not in the OCT-1, MC3T3-E1 or primary osteoblasts (Prim. OB1) lane.

Figure 19A:
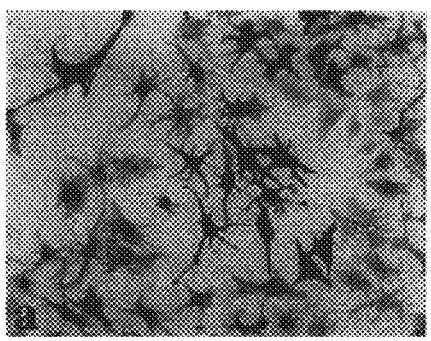
Figure 19A:
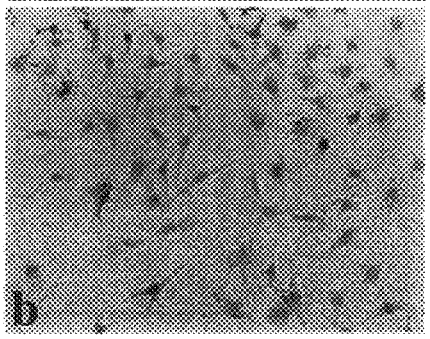

FIG. 19 shows the expression of connexin 43 by immunocytochemistry of MLO-Y4 cells (A). The entire cell surface, including dendritic processes is stained by antibody specific for connexin 43 (a). Non-specific staining using secondary antibody alone (b). Western blot analysis of cell lysate using antibody specific for connexin 43 (B). Equal amounts of protein (10 μg/lane) were loaded into each lane. Brain tissue was used as a positive control. Note the large amount of connexin 43 (MW=43 kDa) compared to the positive control and lack of detectable bands in the osteoblast cell lines and primary cells (Prim. OB1).

FIG. 20 shows the expression of mRNA for osteopontin (A), CD44 (B), type I collagen (C) and OSF-2 (D) in MLO-Y4 cells as compared to other cell types as determined by RT-PCR, using 25 cycles for osteopontin and type I collagen for 30 cycles for CD44 and OSF-2.

FIG. 21 is a table listing the characteristics of the MLO-Y4 cell line as compared to primary osteoblast and to two osteoblast cell lines MC3T3-E1 and OCT-1. t=increased activity in the culture period, ⇆=no change during the culture period, +=detectable, −=not detectable, Western=western blot analysis, EA=enzyme assay, RIA=radioimmunoassay, RT-PCR=reverse transcription polymerase chain reaction analysis.

Figure 22:
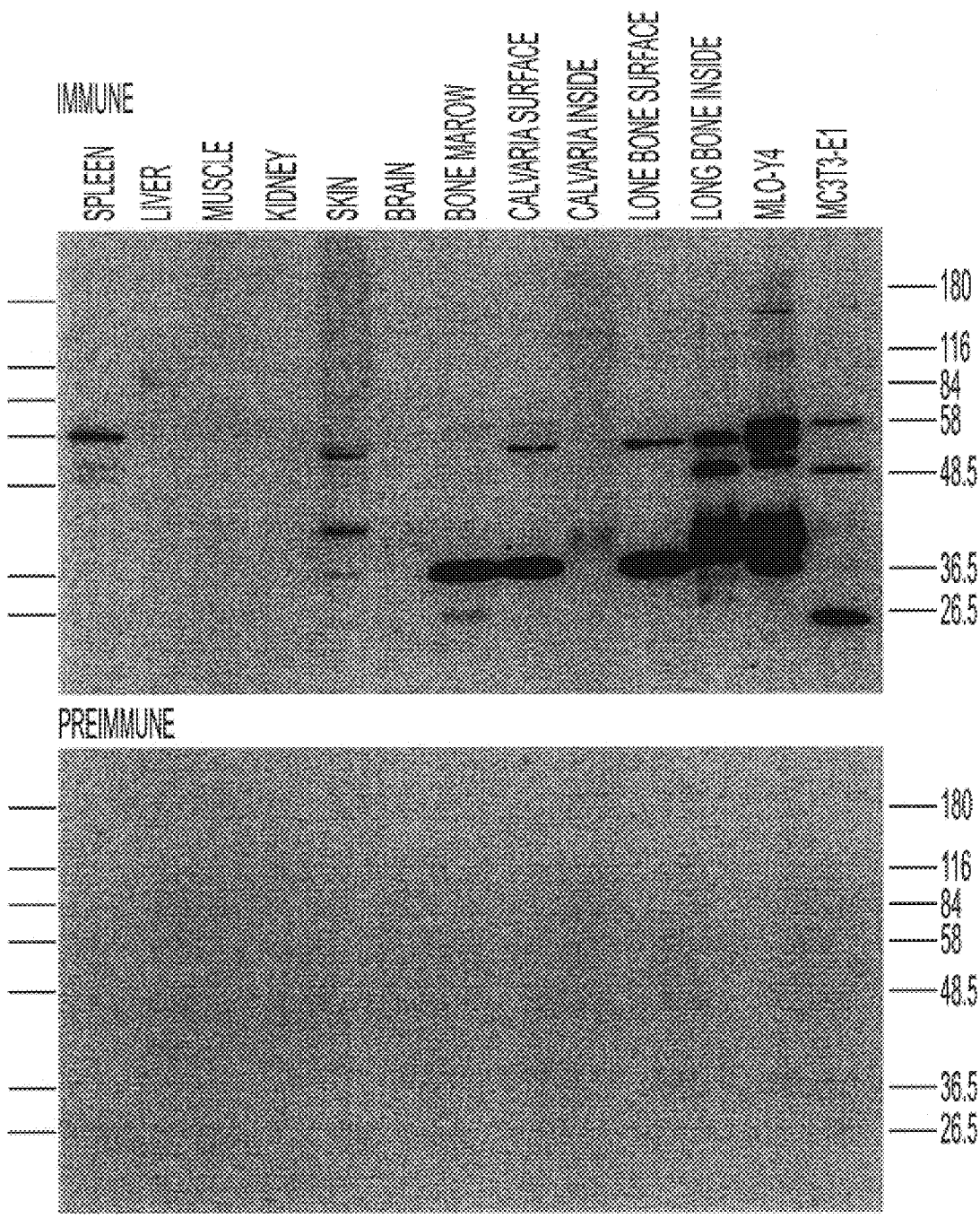

FIG. 22 shows the reactivity of immunized rat serum with a variety of tissues, preparations of primary osteoblast cells from calvaria and long bones, preparations of primary osteocyte cells from calvaria and long bones, and MC3T3-E1 cells. The top panel is a western blot using immune sera and the bottom is the control using preimmune serum.

Figure 23:
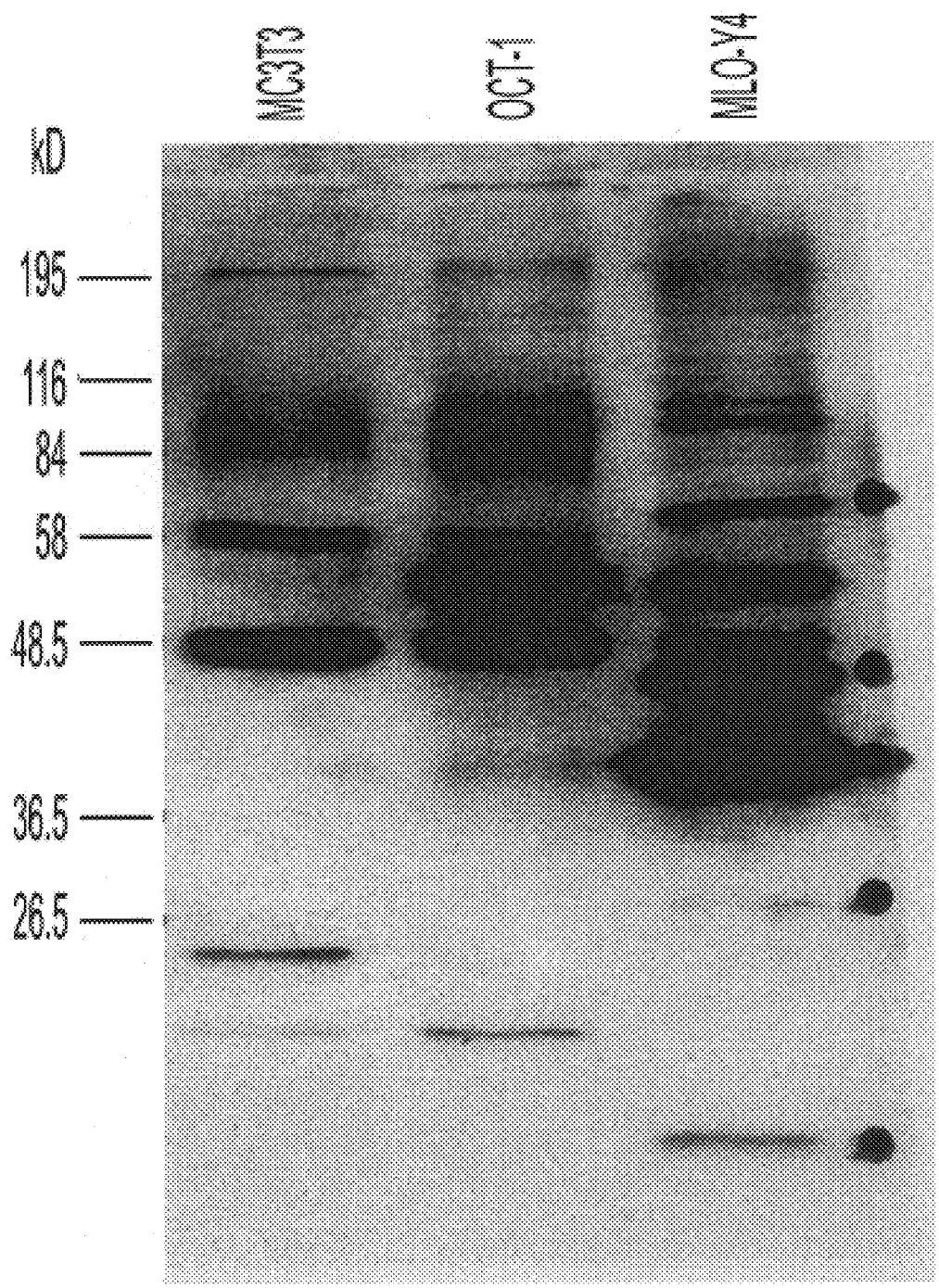

FIG. 23 shows the reactivity of immunized rat serum with MC3T3-E1, OCT-1, and MLO-Y4 cell lysates by western blotting. This is the same rat that was used for generating monoclonal antibodies.

Figure 24:
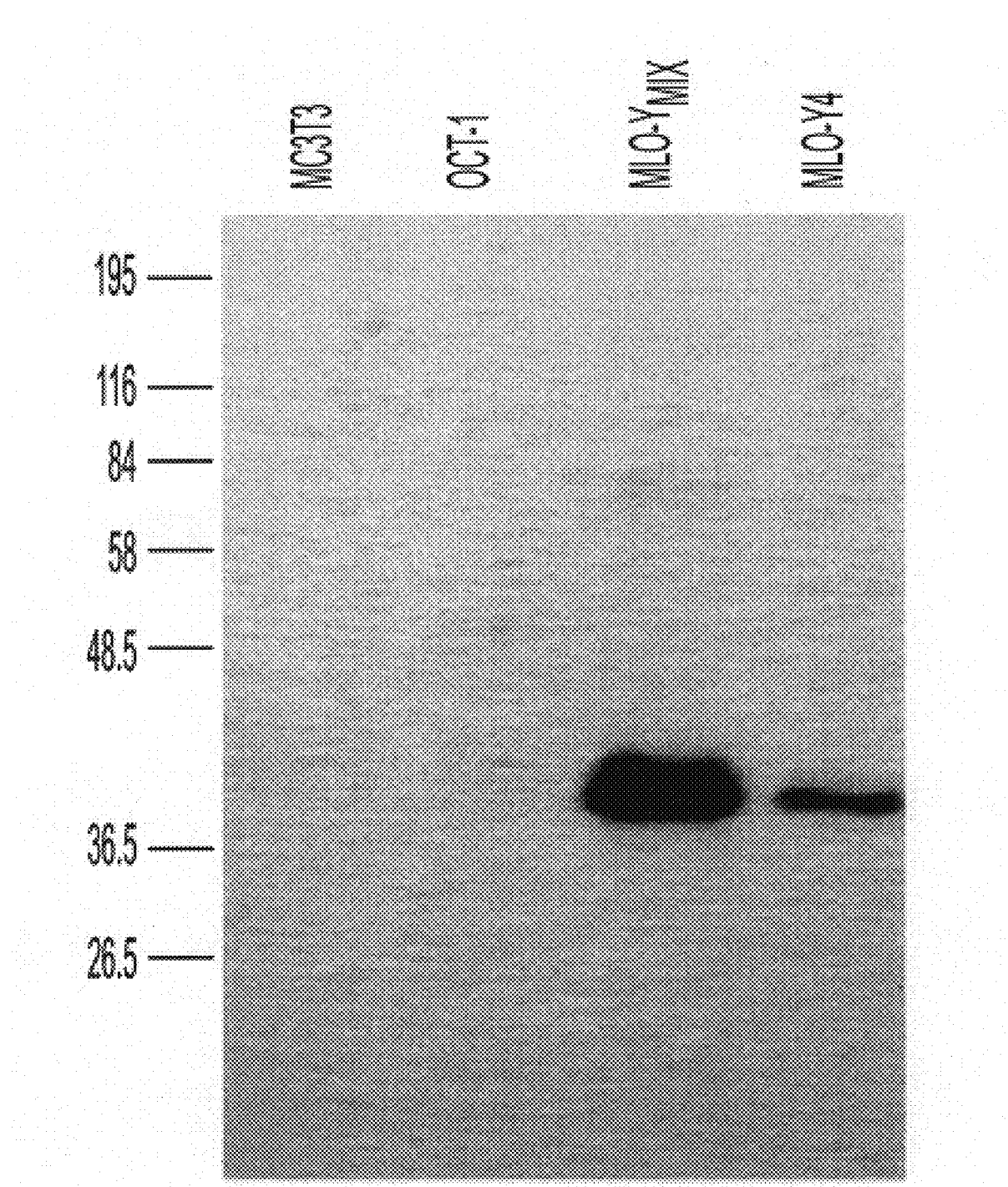

FIG. 24 shows the reactivity of clone 9C11 with MC3T3, OCT-1, MLO-Ymix and MLO-Y4 cell lysates by western blotting.

Figure 25A:
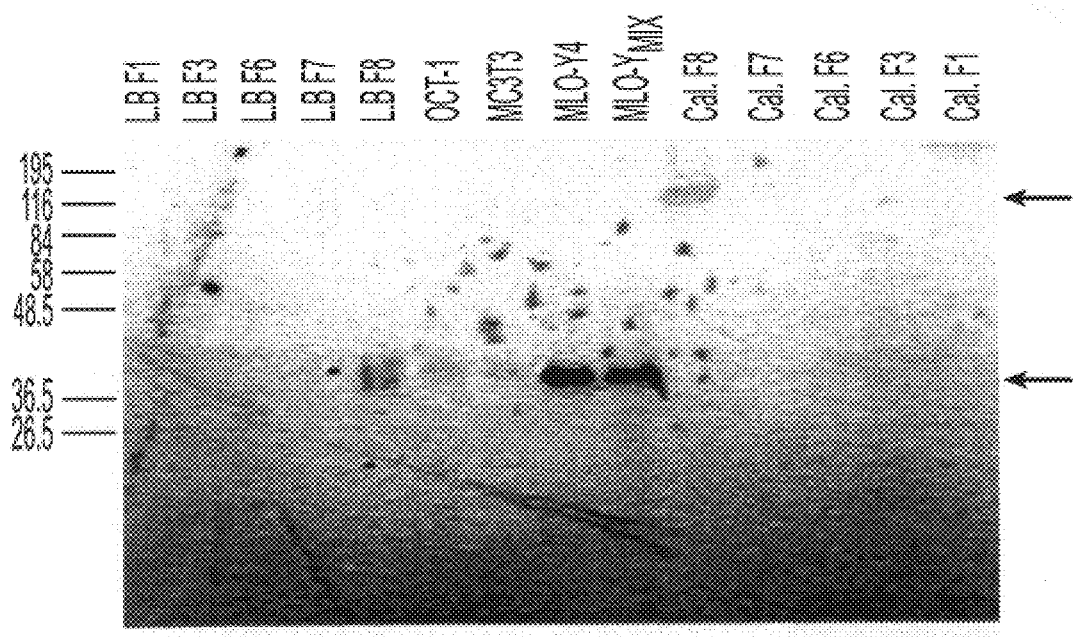
Figure 25B:
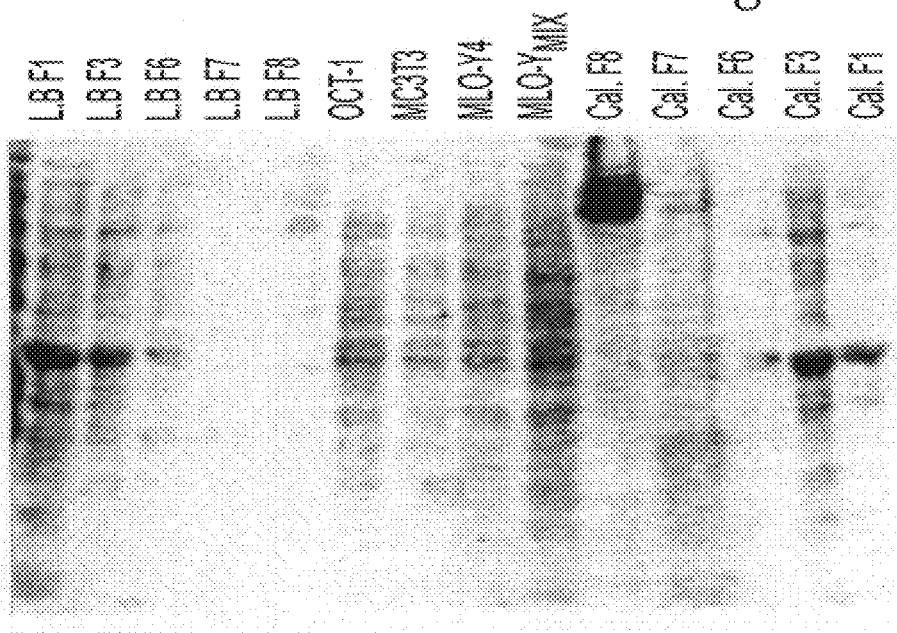

FIG. 25 shows the reactivity of clone 9C11 with long bone lysates (LB), calvarial lysates (Cal.), OCT-1, MC3T3, MLO-Y4 and MLO-Ymix cell lysates by western blotting (A). The gels were also stained with Ponceau S to determine amount of total protein loaded (B).

Figures 26A, 26B:
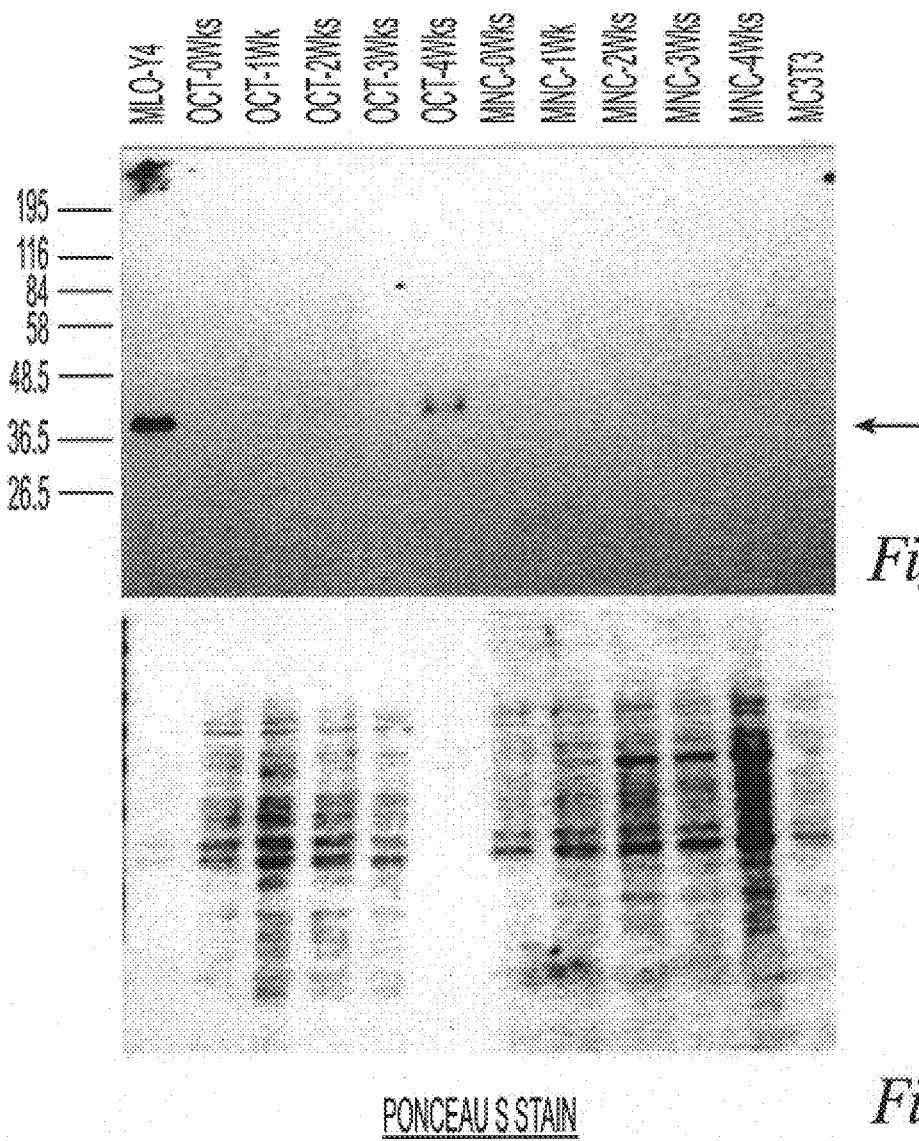

FIGS. 26A and 26B show the induction of the 40 kDa band with treatment of primary mouse osteoblasts, OCT-1 cells, and MC3T3 cells with recombinant BMP-2. (A) shows the western blot using 9C11 supernatant and (B) Ponceau S stain for protein.

Figure 27A:
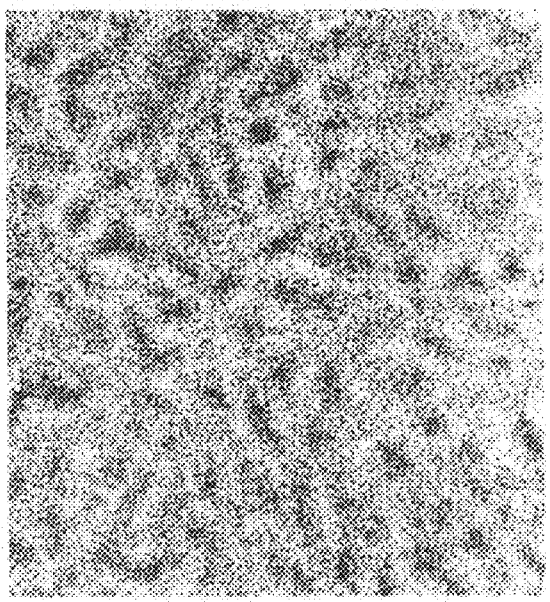
Figure 27B:

FIG. 27 shows the immunohistochemical staining of MLO-Y4 cells with media control (A) and clone 9C11 (B).

Figure 28:
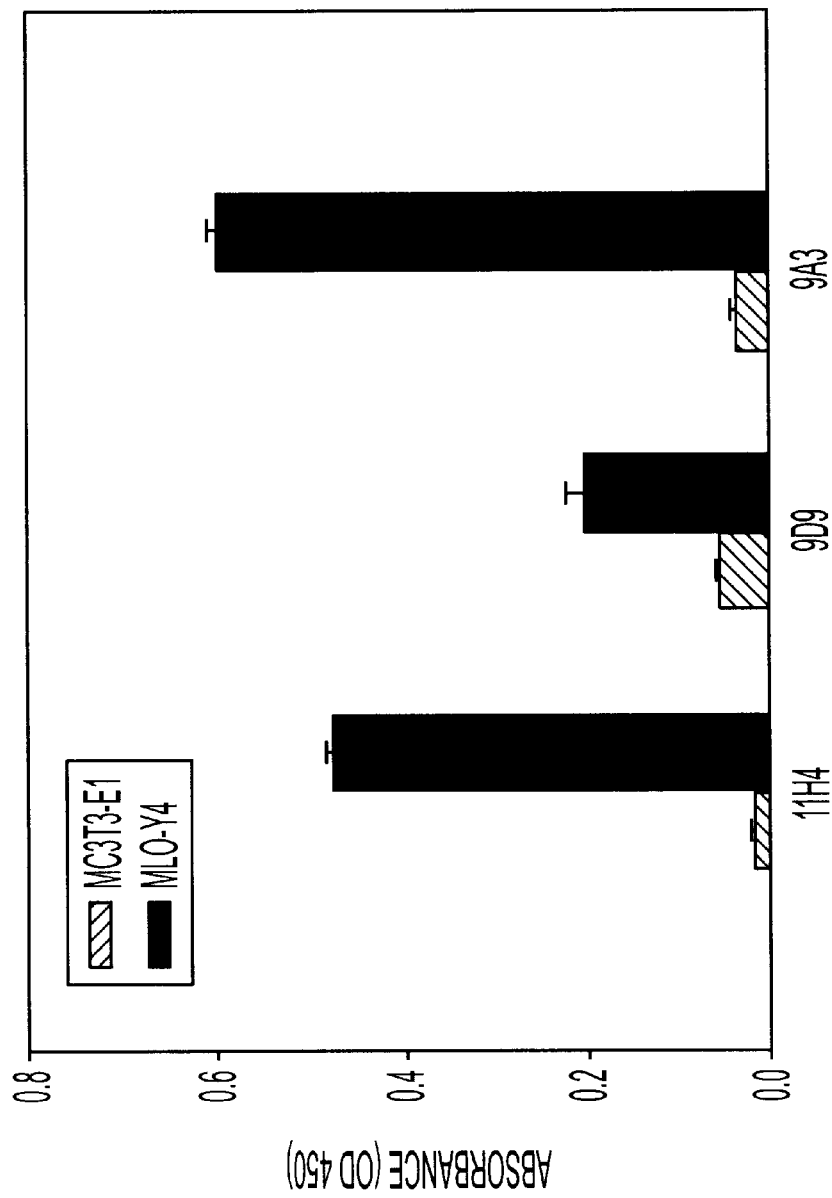

FIG. 28 shows the specificity of clones 11H4, 9D9, and 9A3 for MLO-Y4 cells compared to MC3T3-E1 cells as determined by ELISA.

Figure 29:
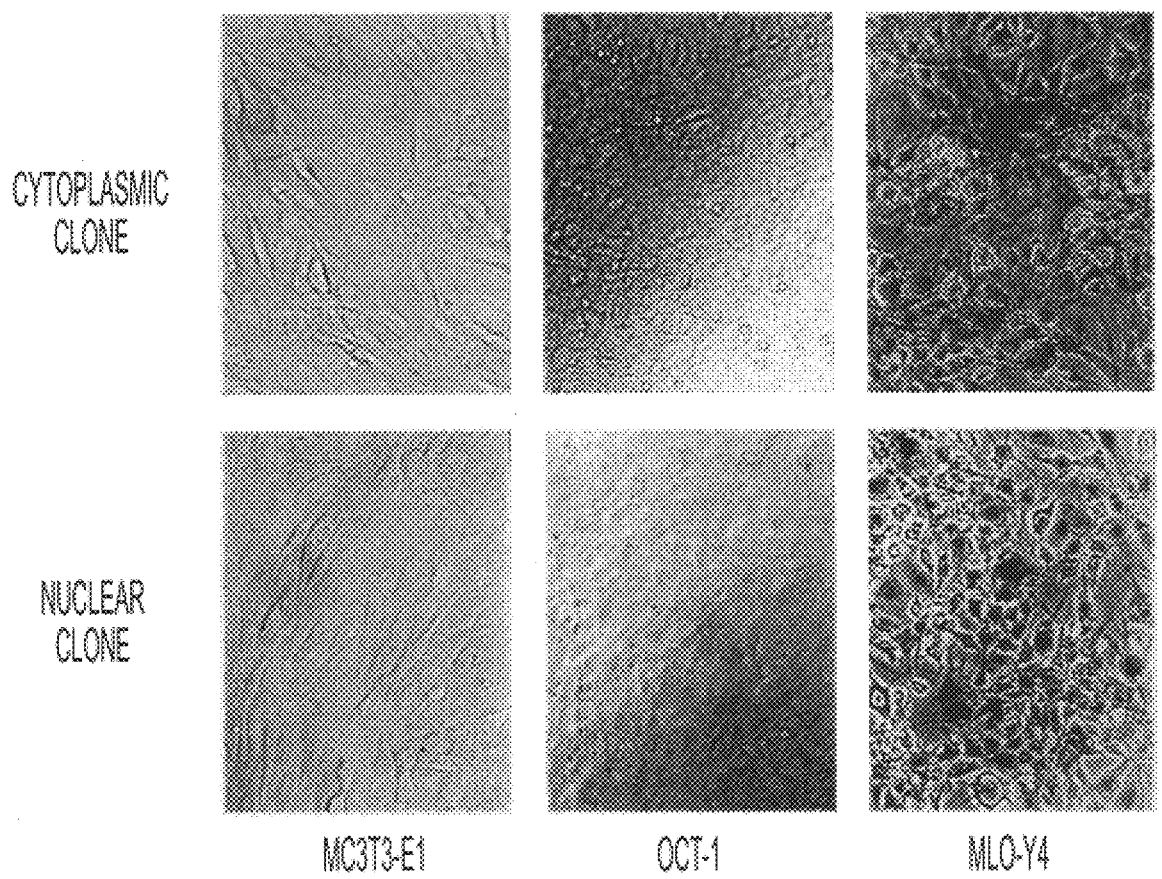

FIG. 29 shows the immunohistochemical staining of MC3T3, OCT-1, and MLO-Y4 cells with clone 11H4 demonstrating cytoplasmic staining of MLO-Y4 cells and staining with clone 9D9 showing nuclear staining of MLO-Y4 cells. OCT-1 and MC3T3 cells are negative.

FIG. 30 shows the immunohistochemical staining of MC3T3, OCT-1, and MLO-Y4 cells with clone 9A3 demonstrating surface staining of both MLO-Y4 and OCT-1 cells while MC3T3 cells are negative.

5. DESCRIPTION OF PREFERRED EMBODIMENT

5.1 Establishment of Transgenic Mice

Construction of the osteocalcin promoter driven T-antigen transgene and establishment of transgenic mice have been described previously (Chen et al., 1995). In short: A 2.6 Kb DNA fragment containing the rat osteocalcin gene promoter region from −2600 to +30 was ligated upstream of the SV40 early region which is containing the protein-coding region of large T- and small T-antigens. DNA was microinjected into the pronuclei of fertilized one-cell mouse embryos. The F2 embryos were derived from matings of CB6F1(C57Bl/6× Balb/c) males and females obtained from Harlan Sprague-Dawley, Inc. (Indianapolis, Ind., U.S.A.). The injected embryos were reimplanted into B6D2F1(C57Bl/6×DBA2) pseudopregnant females. The presence of the transgene in the resulting pups was determined by Southern blot analysis of genomic DNA. Founder transgenic mice were bred to nontransgenic CB6F1 mice to establish the lines of mice.

5.2 Definitions

Osteocyte: stellate shaped with dendritic processes and expresses high level of osteocalcin.

Mature osteocyte: differentiated osteocyte, stellate shaped with dendritic processes and expresses high level of osteocalcin. Also, it expresses low levels of alkaline phosphatase, and type I collagen. It expresses high levels of connexin 43. It does not express OSF-2.

Pre-osteocyte: non-terminally differentiated osteocyte. It does not have the characteristics of mature osteocyte.

FCS: Fetal calf serum

CS: Calf serum

PBS: Phosphate buffered saline

EDTA: Ethylenediaminetetraacetic acid

5.3 Cell Isolation

Seven 14-day old transgenic mice were used for isolation of cells from the long bones. Both ends of the tibiae, femurs and humeri including the growth plate cartilage were cut off, the marrow flushed, leaving the bones which were cut to several pieces. These bone pieces were washed 3× with phosphate-buffered salt solution (PBS), and then the osteocytes isolated according to the method of Mikuni-Takagaki et al., (1995); with several modifications. The bone pieces were sequentially digested 5 times using 0.7 mg/ml collagenase in Hank's balanced salt solution (BSS) for 30 min. at 37° C. Cells were collected with each digestion, (fractions 1 to 5). Additional cell populations were collected after incubation with 4 mM EDTA in PBS (pH 7.5) for 20 min. at 37° C. followed by incubation with 0.7 mg/ml collagenase for 30 min. at 37° C. which was repeated two times (fraction 6 to 9). The bone pieces were washed using PBS at the end of each step. The cells obtained with the washes were combined with each fraction.

Even after these steps, osteocytes still remained in the bone. Therefore the remaining bone pieces were cut into small chips using a scalpel. Released cells and bone chips were plated onto collagen-coated tissue culture plates with α-MEM containing 10% FCS. Most of the cells migrated from the bone pieces after 2 to 3 weeks of culture. These cells were harvested using trypsin-EDTA (fraction 10) and were also used for the cell cloning steps. We also observed that osteocytes were released from trabecular bone along with osteoblast-like cells at the 3rd to 5th collagenase digestions. Therefore, fractions 3 to 5 were also combined (fraction 3–5) and used for cell cloning. (See FIG. 1)

5.4 Cell Culture and Cloning

When the cells were cultured only in FCS, the cells differentiated but did not proliferate and therefore eventually died. However, when the cells were cultured in calf serum, the cells proliferated but did not maintain their osteocytic phenotype. A 50:50 mixture of FCS:CS was found to support cell lines which would proliferate in culture and not lose their dendritic phenotype.

Fractions 3–5 and fraction 10 were cultured on collagen-coated plates in α-MEM supplemented with 5% FCS and 5% CS. After several passages using these culture conditions, osteocytes with the dendritic phenotype were enriched in fractions 3–5. Clonal cell lines were isolated from this osteocytes enriched population (fractions 3–5) and from fraction 10 by single colony isolation. Selection was based on expression of the dendritic phenotype. 16 dendritic cell lines from fraction 10 and 6 dendritic cell lines from fraction 3–5 were cloned.

Tissue culture media were purchased from Gibco BRL (Grand Island, N.Y., U.S.A.), fetal calf serum (FCS) were from BioWhittaker (Walkersville, Md., U.S.A.) and calf serum (CS) and HyClone Laboratories, Inc. (Logan, Utah, U.S.A.). Rat tail collagen type 1, 99% pure, was purchased from Becton Dickenson Lab. (Bedford, Mass.). All other reagents were purchased from Sigma Chemical Co. (St. Louis, Mo., U.S.A.) unless otherwise stated.

Clones were selected from fraction 10 based upon osteocyte morphology (See FIG. 2). Various morphologies were observed ranging from very small stellate cells to cells with extensive processes sometimes many times longer than the cell body. These clones are denoted as MLO-A to MLO-F (MLO stands for 'murine long bone osteocytes'). A cell line is established when the cells maintain a stable homogeneous morphology after more than 20 passages.

Figure 7:
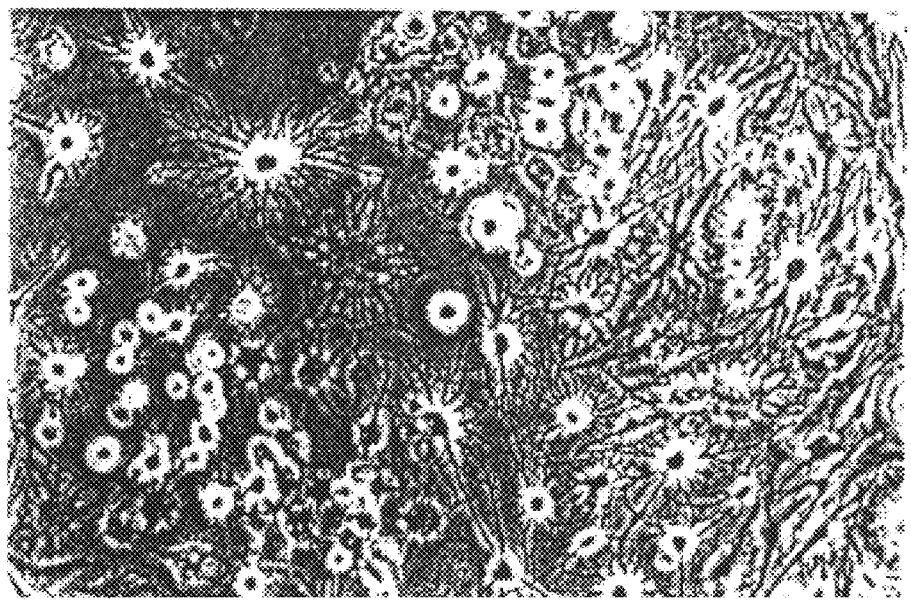
FIG. 7 is a picture of the cultured osteocyte:MLO-Y from fractions 3–5.

Cultures were also maintained from fractions 3–5. Originally very few dendritic cells were present in these cultures, however after several months culture in 50% FCS, 50% CS, highly dendritic cells were observed. Cells were selected from fraction 3–5 and a representative picture of the cultured osteocyte:MLO-Y is shown in FIG. 7, cells cloned from MLO-Y are denoted as the MLO-Y series.

5.5 Establishment of an Osteocyte Cell Line From Cultured Osteocyte:MLO-Y

Figures 14A, 14B, 14C, 14D, 14E, 14F:
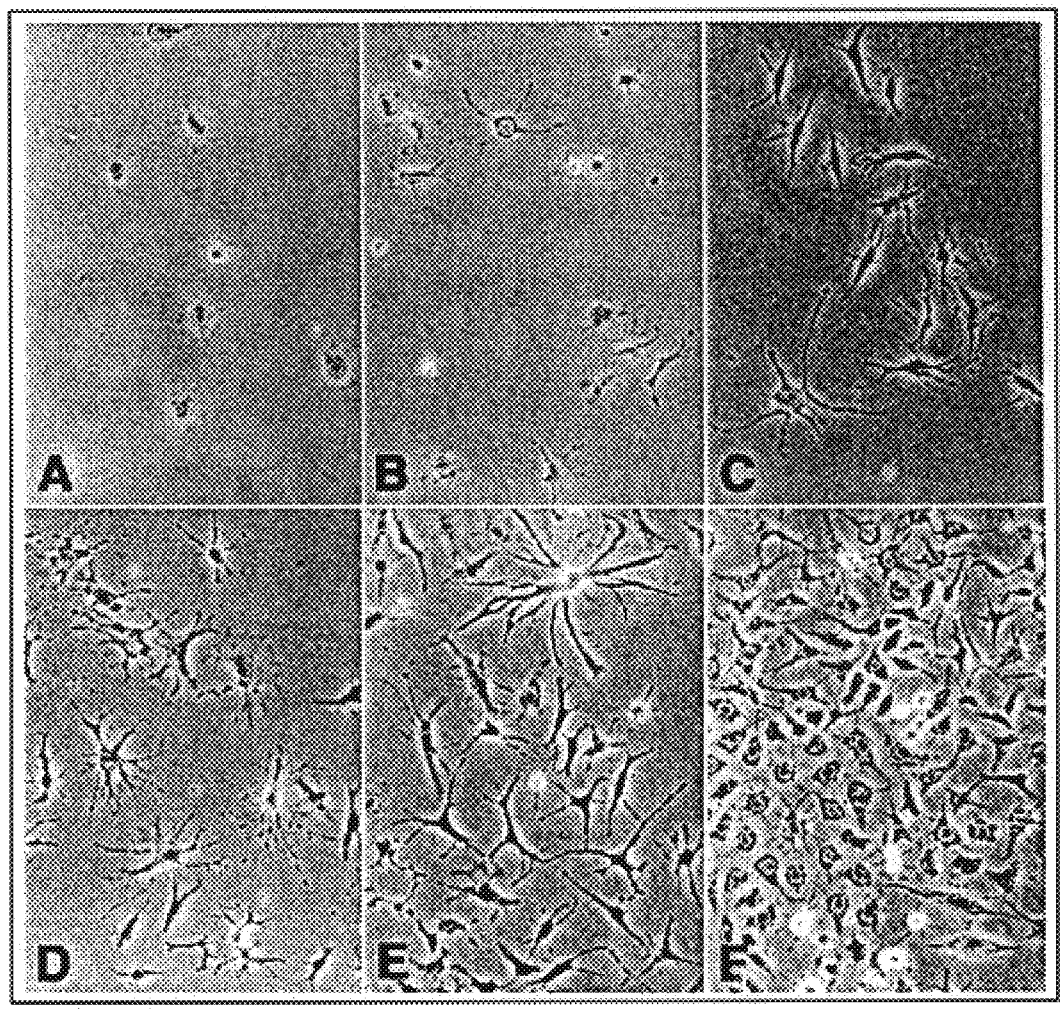

The MLO-Y4 cell line was cloned from this MLO-Y population by single colony isolation. Selection was based on expression of the dendritic phenotype. To examine morphological changes with growth and proliferation, MLO-Y4 cells were plated on collagen coated surfaces at low density, and were observed by phase-contrast-microscopy over time (FIG. 14). These cells adhere very rapidly to substrate and after 3 to 6 hours, the cells were small and stellate in shape with many short processes (FIGS. 14A–B). After 1 to 2 days, these processes became elongated, and began to branch (FIGS. 14C–E). In the confluent phase, the cellular processes continued to make contact with other cells (FIG. 14F). These cells have maintained this homogeneous morphology after more than 45 passages.

5.6 Measurement of Cellular Proliferation $2 \times 10^3$ cells were plated on collagen-coated or non-coated 48 well plates, and cultured with α-MEM+5% FCS/5% CS or α-MEM+10% FCS. Media were changed every 3 days. Cell cultures were stopped after 1, 3, 4, 5, 7, 8, or 10 days, and the cells were harvested after trypsin-EDTA treatment. Cell number was measured using a Coulter Counter, model ZF (Coulter Electronics, Inc. Hialeah, Fla., U.S.A.).

Figure 16A:
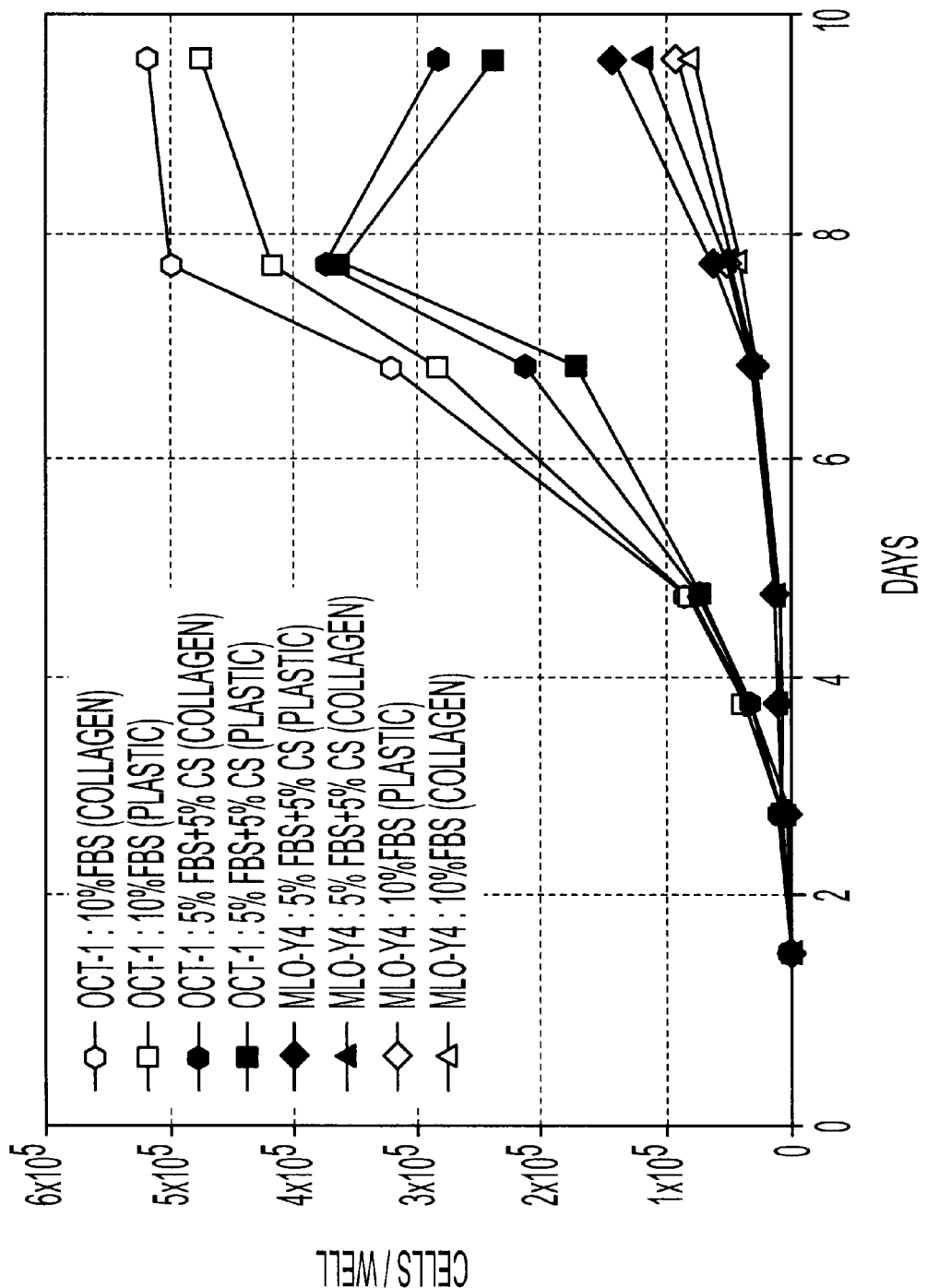
Figure 16B:
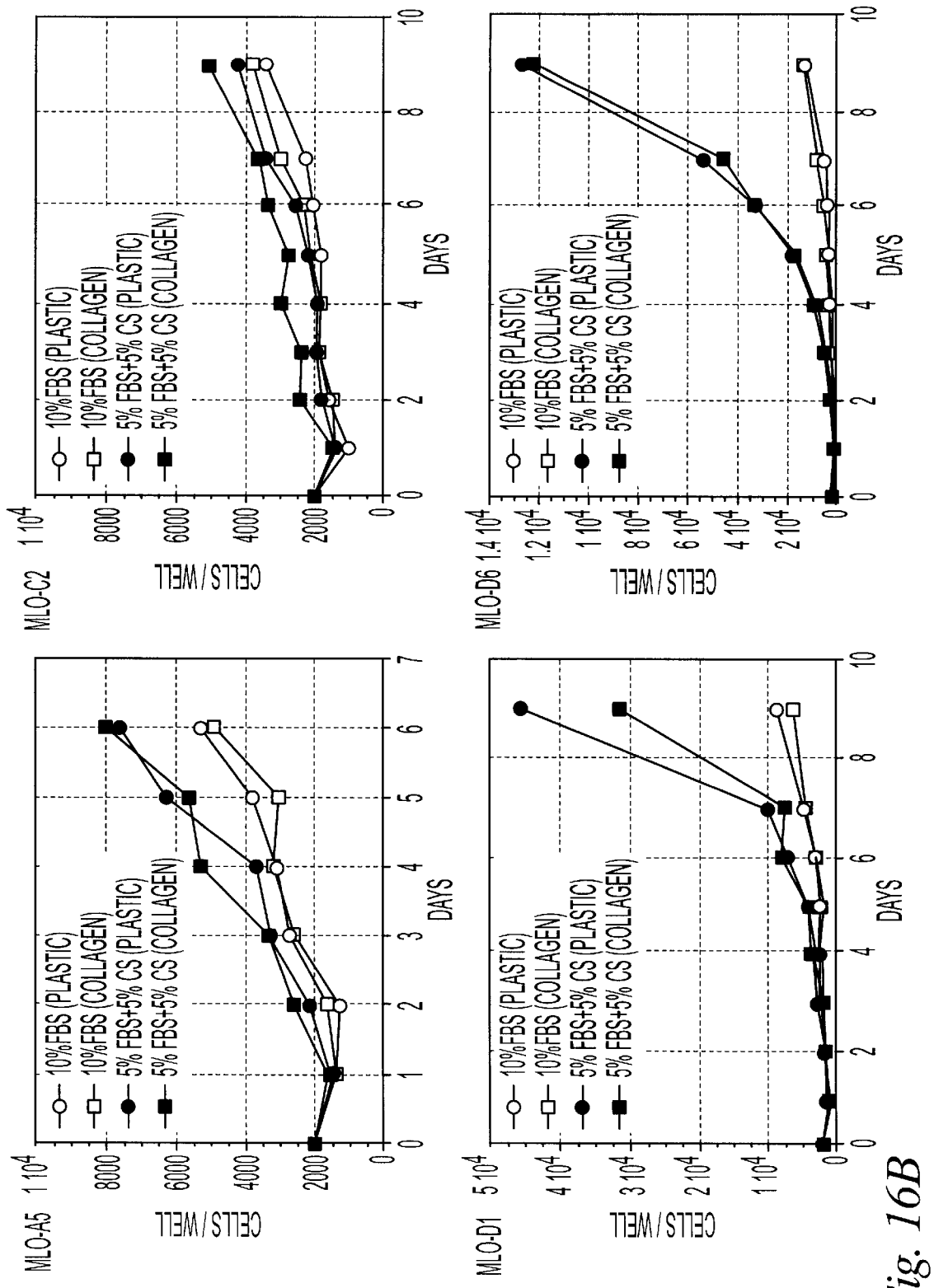

The proliferation rate of the MLO-Y4 cell line was also determined and compared to the osteoblast-like cell line, OCT-1, using collagen coated and plastic surfaces and 10% FCS-supplemented medium compared to 5% FCS/5%CS. OCT-1 was established from the same type of transgenic mouse, the osteocalcin promoter driven T-antigen mouse, as MLO-Y4 cells (Chen et al., 1995). The MLO-Y4 cells grew faster with 5% FCS/5% CS than with 10% FCS. OCT-1 cells grew faster in 10% FCS compared to 5% FCS/5% CS. On the other hand, MLO-Y4 growth on the collagen surface was slightly suppressed compared to plastic. This could be due to greater expression of the dendritic morphology on collagen surfaces using either 5% FCS/5% CS or 10% FCS containing media (FIG. 16A). The proliferation rate of the MLO-A to MLO-D cell lines were determined. MLO-A to MLO-D cells also grew faster with 5% FCS/5% CS than with 10% FCS (FIG. 16B).

5.7 Determination of T-antigen Expression by Western Blot Analysis

T-antigen protein expression in these cell lines was determined by Western blot analysis according to a previously described technique (Bonewald et al., 1989). Subconfluent cells were washed 2× with PBS and lysed by ice cold RIPA buffer (50 mM Tris-HCl, pH 7.2, 150 mM NaCl, 1% NP-40, 0.5% sodium deoxycholate) 5 min. incubation at 4° C. The lysates were collected and centrifuged at 14,000 rpm for 10 min and the supernatant collected. The aliquots of each sample were treated with 2× electrophoresis sample buffer containing reducing agent and applied to 10% SDS-PAGE. Proteins were transferred onto a nitrocellulose membrane by electroblotting (Bonewald et al., 1991). The membranes were blocked with 5% BSA in TBS buffer (50 mM Tris-HCl, 150 mM NaCl, pH 7.4) over night at 4° C. Mouse anti-SV40 T-antigen monoclonal antibody (Oncogene Science, Inc., Cambridge, Mass., U.S.A.) was diluted 1:50 in TBS buffer+1% BSA for the primary antibody solution. Peroxidase-conjugated goat anti-mouse IgG Fc antibodies were used at a 1:2000 dilution in TBS buffer+5% skim milk for the secondary antibody solution. The blot was washed 5× with TBS+0.05% Triton X-100 between each step. Bands were visualized using the chemiluminescence detection system as described by the manufacturer (DuPont NEN Research Products, Boston, Mass., U.S.A.). The MYO-Y4 cells were positive to T-antigen expression by Western blot analysis (FIG. 15). All of the MLO-A to MLO-F clones from fraction 10 and cultured osteocyte:MLO-Y also expressed T-antigen (FIG. 8).

5.8 RNA Preparation and RT-PCR Analysis

Total cellular RNA was isolated from cultures of confluent cells using RNAzol™ B(Biotecx Laboratories, Inc., Houston, Tex., U.S.A.) according to manufacturer's instructions. One of 10 cm confluent culture plate was used for MC3T3-E1 and OCT-1 and 4 to 8 confluent 10 cm culture plates were used for MLO-C2, MLO-D6 and MLO-Y4, cDNAs were synthesized from 3 μg of total RNA in a 20 μl reaction mixture containing 1× reverse transcriptase buffer (Promega, Madison, Wis., U.S.A.), 0.26 U/μl RNase inhibitor (Promega), 500 μM dNTP mixture, 10 mM DTT, 50 pmol of oligo d(T)16 primer (Perkin Elmer, Norwalk, Conn., U.S.A.) and 20 U of AMV reverse transcriptase (Promega). 0.5–2% of cDNA was amplified using polymerase chain reaction in a 20 μl reaction mixture containing 1× PCR buffer (Fisher Scientific, Pittsburgh, Pa., U.S.A.), 5 pmol of 5' and 3' primer, 200 μM dNTP mixture, 2 mM $MgCl_2$ (Fisher Scientific) and 1 U of Taq DNA Polymerase (Fisher Scientific). Amplifications were performed in a DNA Thermal Cycler 480 (Perkin Elmer Cetus, Emeryville, Calif., U.S.A.) for 30–35 cycles following the reaction profile: 94° C. for 1 min., 55–60° C. for 1.5 min. and 72° C. for 2 min.

The following primers and annealing temperatures were used for each particular cDNA amplification.

```
5V40 T-antigen:            5'-AGCAGACACTCTATGCCTGTGTGGAGTAAG
                           3'-GAGTCAACGTAGGGTCTTCGGAGGTTTCAG; 60° C.
Mouse osteocalcin:         5'-GACAAAGCCTTCATGTCCAAGC
                           3'-GTTTGAGACCGTCGAGCCGAAA; 58° C., 25 cycles
Mouse osteopontin:         5'-GACCATGAGATTGGCAGTGATTTG
                           3'-GTTTCGGTCGGACCTTGTAGT; 58° C.,25 cycles
Mouse O5F-2:               5'-TGGAAGGGATGAAAGGCTGC
                           3'-CGGTGTTTACCACAGCAGGT; 58° C.,30 cycles
Mouse collagen I:          5'-AATGGTGAGACGTGGAAACCCGAG
                           3'-GGTTTGAGTCTTCTACATCCTCAGC; 58° C., 25 cycles
Mouse estrogen receptor:   5'-TGGCTACCATTATGGGGTCTGG
                           3'-CTTGGCGGGTACTAGATAAGAC; 57° C.
Mouse actin:               5'-CCAACCGTGAAAAGATGACCC
                           3'-GTGATAACCGTTGCTCGCCA; 57° C.
Mouse CD44:                5'-CAAGTTTTGGTGGCACACAGC
                           3'-GGTTAAGGAAGCTACCTGGC; 58° C.,30 cycles
```

Reaction products were analyzed by 1.5% agarose gel electrophoresis with ethidium bromide staining.

5.8.1 Osteocyte Cell Lines Express Similar Amounts of Osteopontin and CD44 MRNA Compared to Osteoblasts As osteocytes have been reported to express osteopontin, a major matrix protein (Hirakawa et al., 1994) and CD44, a neural antigen, (Hughes et al., 1994; Nakamura et al., 1995), we examined MLO-Y4 cells for expression of these molecules by RT-PCR. Osteopontin and CD44 MRNA were expressed by both MLO-Y4 and osteoblast-like cells (FIGS. 20A, B).

Figures 20A, 20B, 20C, 20D:
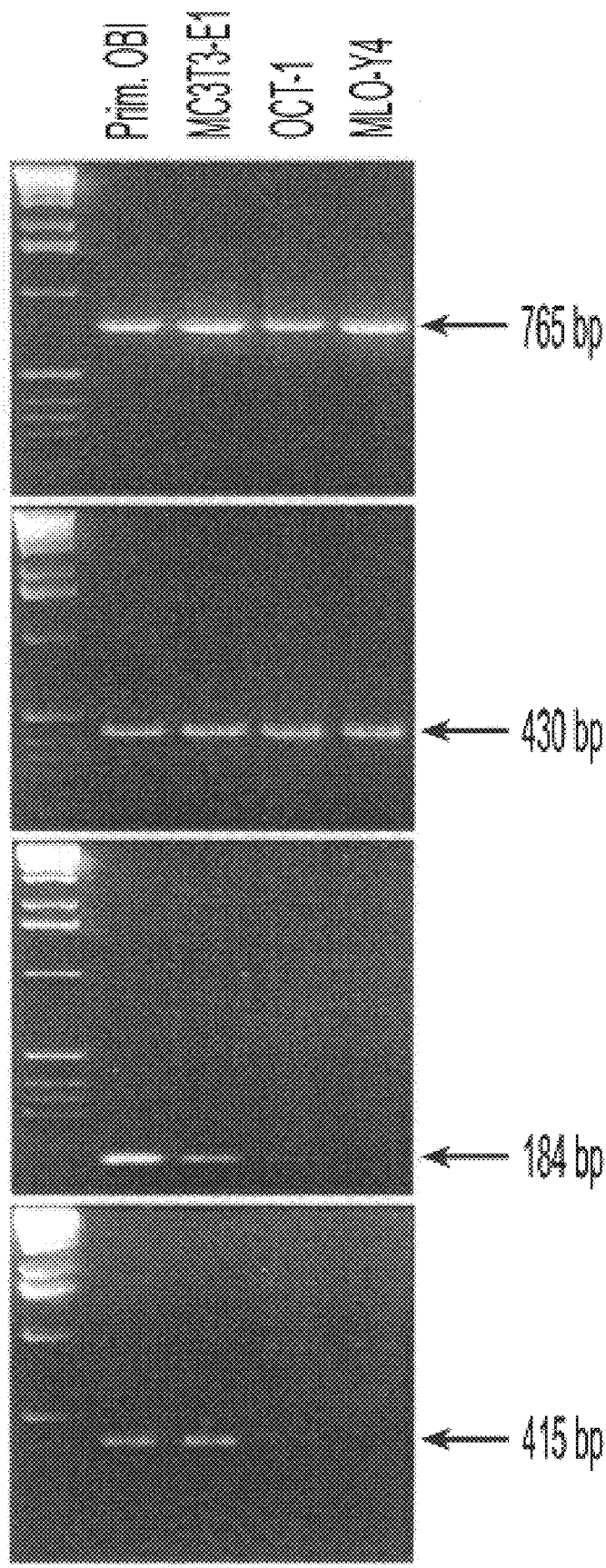

5.8.2 Osteocyte Cell Lines Express Low Amounts of Type I Collagen mRNA Compared to Osteoblasts Type I collagen mRNA expression in MLO-Y4 was not detectable by RT-PCR for 25 cycles, whereas bands were clearly present in osteoblast-like cells (FIG. 20C). When RT-PCR conditions were extended to 30 cycles, the band corresponding to type I collagen was faint but detectable in MLO-Y4 cells (data not shown). This suggests the MLO-Y4 cells express low levels of type I collagen compared to osteoblast-like cells.

5.8.3 Osteocyte Cell Lines Do Not Express Osteoblast-Specific Factor 2 (OSF-2)

OSF-2 was recently cloned from an MC3T3-E1 library and is expressed by primary osteoblasts, by MC3T3-E1 cells and in lung tissue as shown by Takeshita and coworkers (Takeshita et al., 1993). OSF-2 is proposed to be an osteoblast marker; therefore, RT-PCR was performed to determine if MLO-Y4 cells also express this protein. We found that MLO-Y4 cells do not express any detectable OSF-2 mRNA by RT-PCR using 30 cycles. In contrast, a band corresponding to OSF-2 was obvious in the osteoblast-like cells MC3T3-E1, OCT-1 cells and primary osteoblasts (FIG. 20D). The same results were obtained when the number of PCR cycles was increased to 35 (data not shown).

The two faint upper bands in the MLO-Y4 lane (FIG. 20D) were sequenced.

Sequence Analysis of PCR Products

The bands of interest were excised from the gels and TA cloned into pGEM-T vector per suppliers instructions (Promega, Madison, Wis.). Transformation followed by an insertion check was performed before DNA sequencing using a kit for dye terminator cycle sequencing (Perkin-Elmer, Norwalk, Conn.) which was then read using an Applied Biosystems model 373A DNA sequencer. Although they contained the PCR primer sequences, they had no homology to OSF-2. One band had high homology to human transducin-like protein and the second had no significant homology to any known protein, whereas the OSF-2 band in the osteoblast lanes was 100% homologous to the OSF-2 sequence. The upper two bands may have been transcribed more efficiently in the OCT-1 and MLO-Y4 cell lines as little (OCT-1) or no (MLO-Y4) OSF-2 mRNA was available for transcription.

The characteristics of the MLO-Y4 cell line are summarized and compared with osteoblast-like cells in FIG. 21.

5.9 Quantitation of Osteocalcin by Radioimmunoassay (RIA)

Cells were plated on collagen coated 48 well plates. After 3 days of culture with α-MEM+10% FCS or α-MEM+5% FCS+5% CS, the conditioned media in each subconfluent well was harvested. Osteocalcin in these conditioned media was measured using a mouse osteocalcin RIA kit according to manufacturer's instructions (Biomedical Technologies Inc.: Stoughton, Mass., U.S.A.).

5.9.1 Osteocyte Cell Lines Express High Levels of Osteocalcin

MLO-Y4 and MLO-Y2 cells secreted very high levels of osteocalcin into conditioned medium within only 3 days culture (MLO-Y2:14.5 ng.ml; MLOY-4:11.80 ng/ml with 10% FCS and 11.25 ng/ml with 5% FCS/5% CS) while osteoblast-like cells expressed barely detectable osteocalcin during this same culture period (primary osteoblasts: 0.9 ng/ml; MC3T3-E1:1.9 ng/ml; and OCT-1:15 ng/ml with 10% FCS) MLO-A to MLO-F cell lines also secreted high levels of osteocalcin into conditioned medium (6–12 ng/ml) (FIG. 18A). RT-PCR results supported observations made using the osteocalcin RIA. Osteocalcin mRNA was present in MLO-Y4, however primary osteoblast cells, MC3T3-E1 and OCT-1 did not present detectable osteocalcin mRNA under identical RT-PCR conditions (FIG. 18B). All of the MLO-A to MLO-F cell lines and cultured osteocyte:MLO-Y express osteocalcin (FIG. 8).

5.10 Determination of Connexin 43 Expression by Immunocytochemical Staining

Subconfluent cells in 48 well culture plates were fixed using 3% paraformaldehyde and 2% sucrose in PBS and permeabilized with 0.05% Triton X-100. The fixed plates were blocked with 5% BSA in TBS buffer for 2 hours at room temperature. These cells were then incubated with a 1:125 dilution of anti-connexin 43 monoclonal antibody (Zymed Laboratories, Inc., San Francisco, Calif., U.S.A.) in TBS buffer+1% BSA for 2 hours at room temperature. The bound antibody was detected using Vectastain ABC Kit, followed by staining with VIP substrate according to manufacturer's instructions. (Vector Laboratories, Burlingam, Calif., U.S.A.). The counter staining was performed using 0.5% methyl green, and the secondary antibody was used alone as a control for background staining. The procedure as listed above as used for T-antigen expression was used for anti-connexin 43 western blot analysis. The specific antibody for murine connexin 43 was obtained from Zymed Laboratories and used at a 1:1000 dilution. Ten percent SDS-PAGE was used.

5.10.1 MLO-Y4 Cells Express Large Amounts of Connexin 43

Figure 19B:
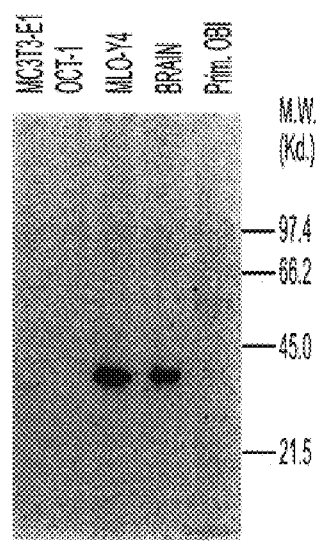

Because it has been shown in situ that osteocytes express connexin 43, a gap junction protein (Mason et al., 1996), we examined MLO-Y4 cells for expression of this protein important for cell-cell communication. MLO-Y4 was strongly positive by Immunocytochemistry using anti-connexin 43 antibody (FIG. 19A). Staining was found in the cytoplasm and along the long dendritic processes. Strong staining was also observed around the nucleus in some cells. Western blot analysis was also used to compare MLO-Y4 cells to osteoblast-like cells for expression of connexin 43. Connexin 43 was detected in MLO-Y4 cell lysates from both 10% FBS and 5% FBS/5% CS culture conditions. The band in the MLO-Y4 lane was stronger than mouse brain tissue lysate which was used as positive control. In contrast, mouse primary osteoblast cells, MC3T3-E1 and OCT-1 cell lysate were negative although equivalent amounts of protein was loaded (FIG. 19B).

Figure 17A:
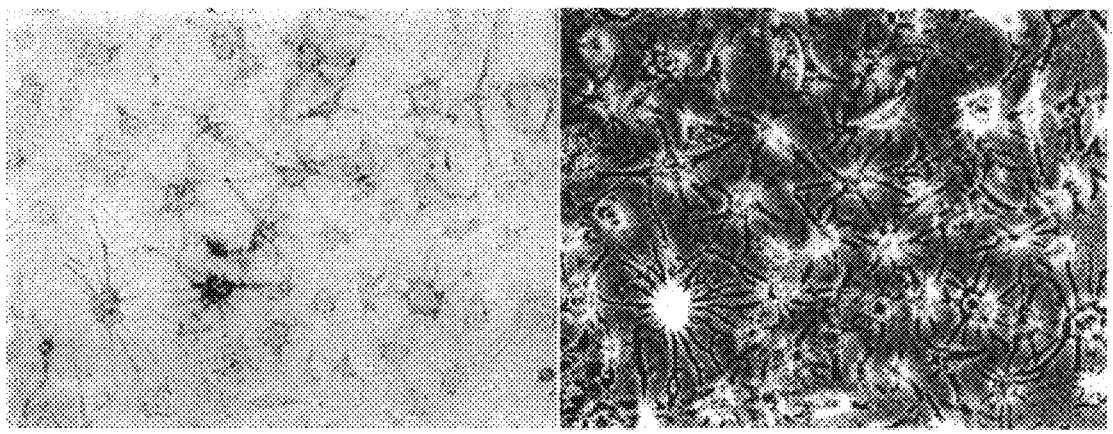
Figure 17B:
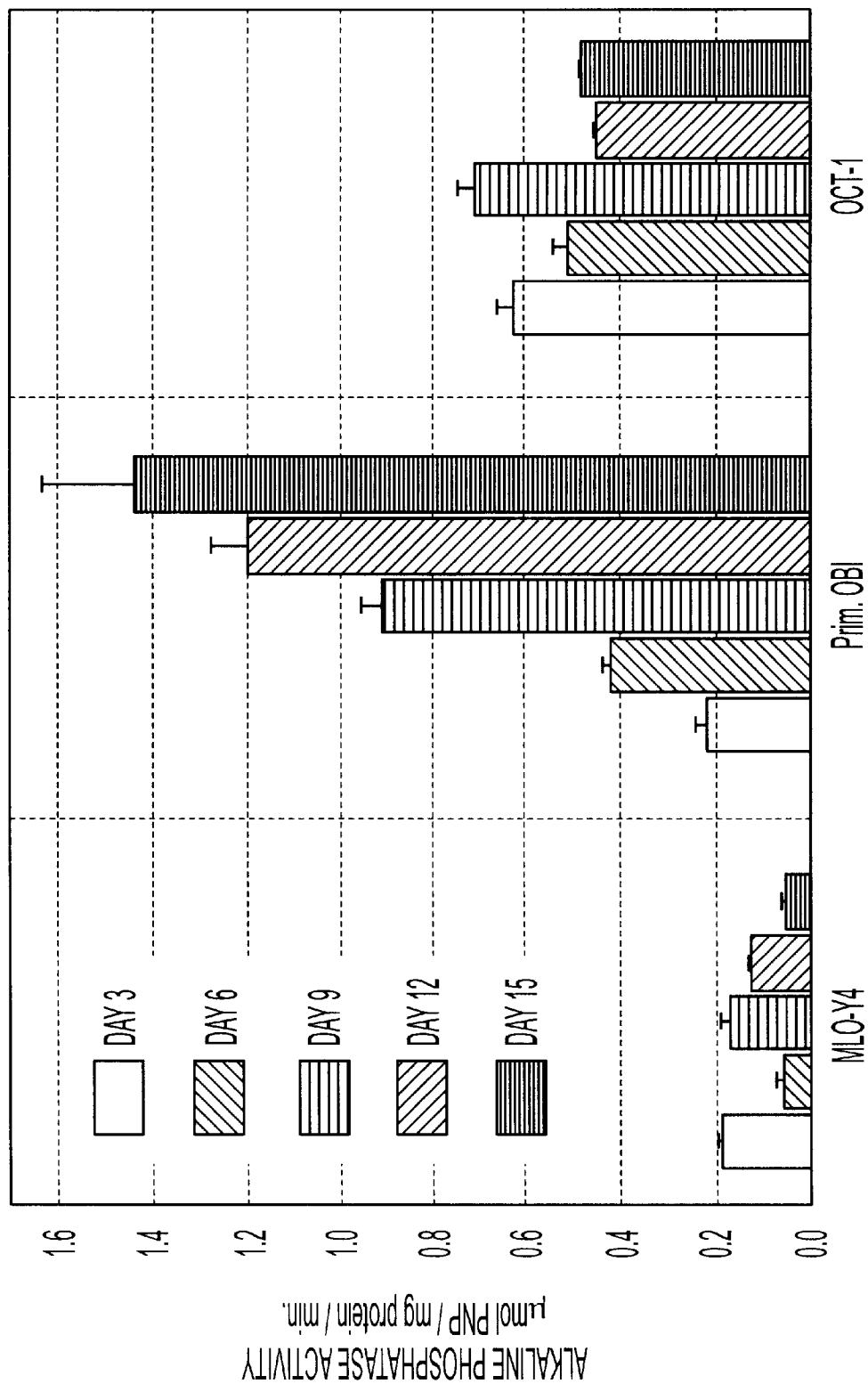

5.11 Staining for Alkaline Phosphatase Activity $1\times10^8$ cells were plated on each collagen-coated 10 cm culture dish. After 3 to 7 days culture, MLO-Y4 cells were fixed by 10% buffered formalin for 10 min. After washing 2× with PBS, freshly prepared 0.033% nitro blue tetrazolium (NBT) and 0.017% bromochloroindoyl phosphate (BCIP) in alkaline phosphatase buffer (100 mM NaCl, 5 mM $MgCl_2$, 100 mM Tris-HCl, pH 9.5) was added to the fixed cells, and incubated for 15 min. at 37° C. Reaction was stopped by washing with running water. Stained cells were observed using 25× and 50× magnification on an Olympus CK2 microscope. Cells were negative, with only weak staining in the cytoplasm of a small number of cells (FIG. 17A).

Figure 3:
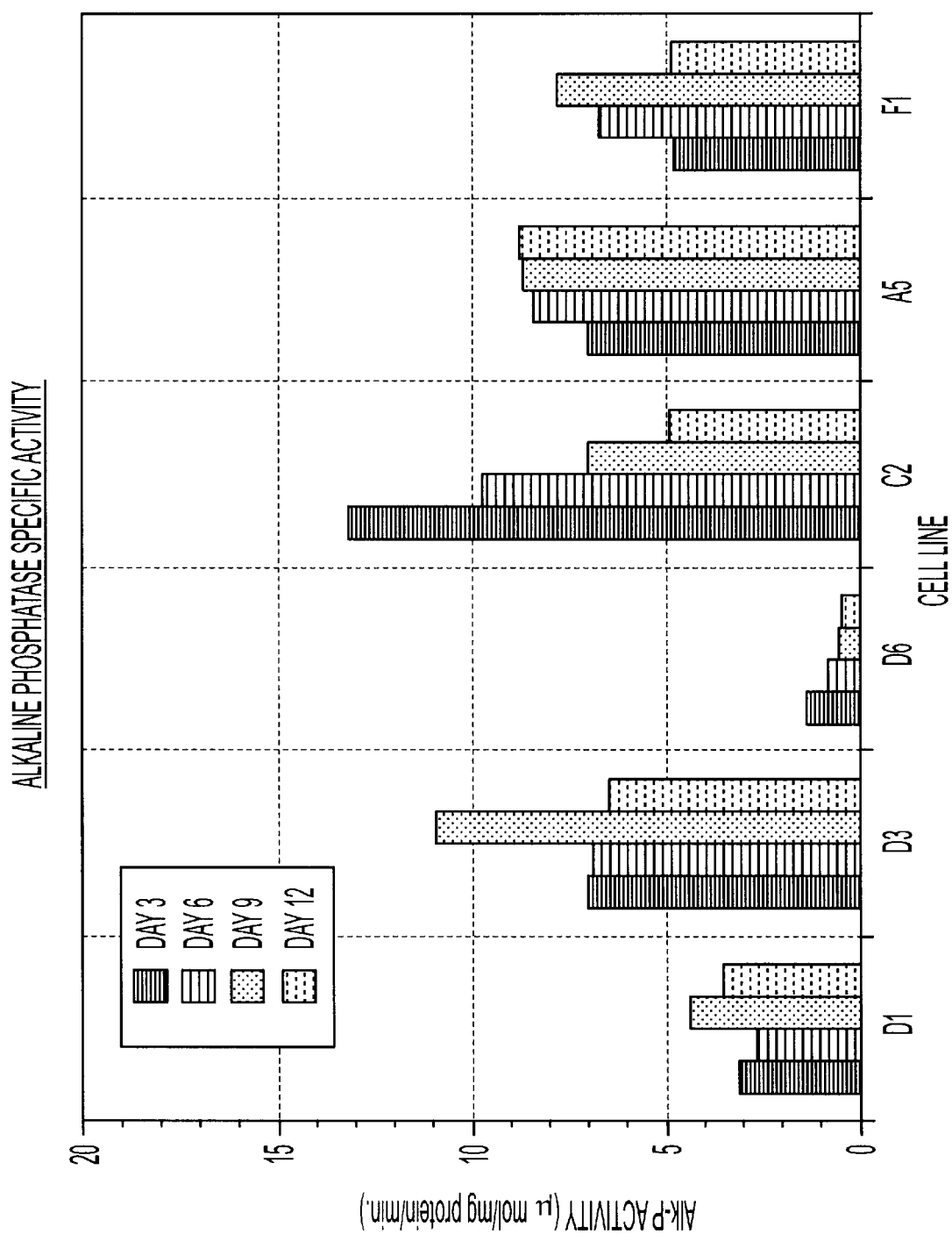
FIG. 3 shows the alkaline phosphatase specific activity of cell lines derived from fraction 10 after 12 days of culture.
Figure 10:
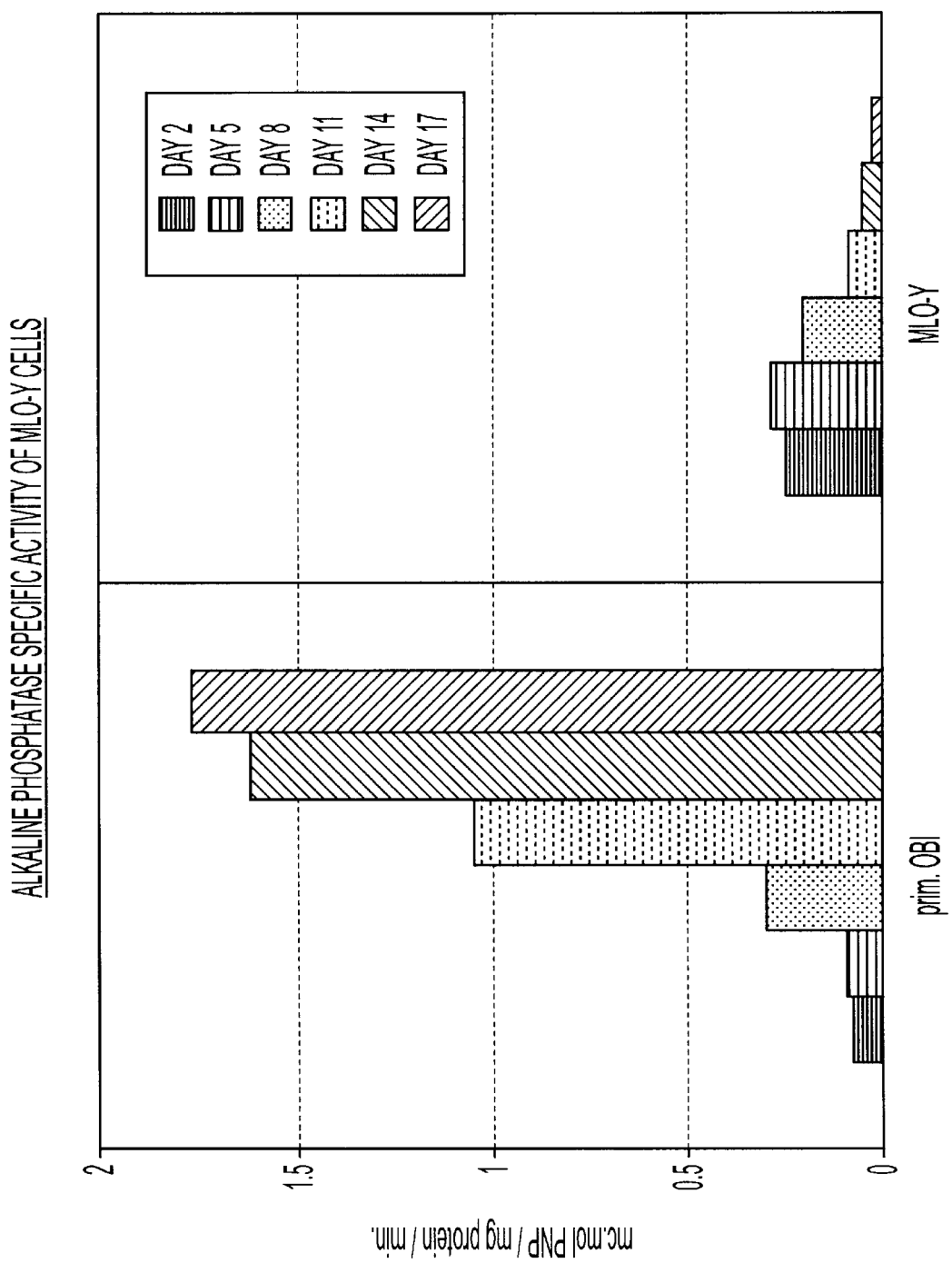
FIG. 10 shows the alkaline phosphatase specific activity of cultured osteocyte as compared to primary osteoblasts with culture over 17 days.
Figure 13:
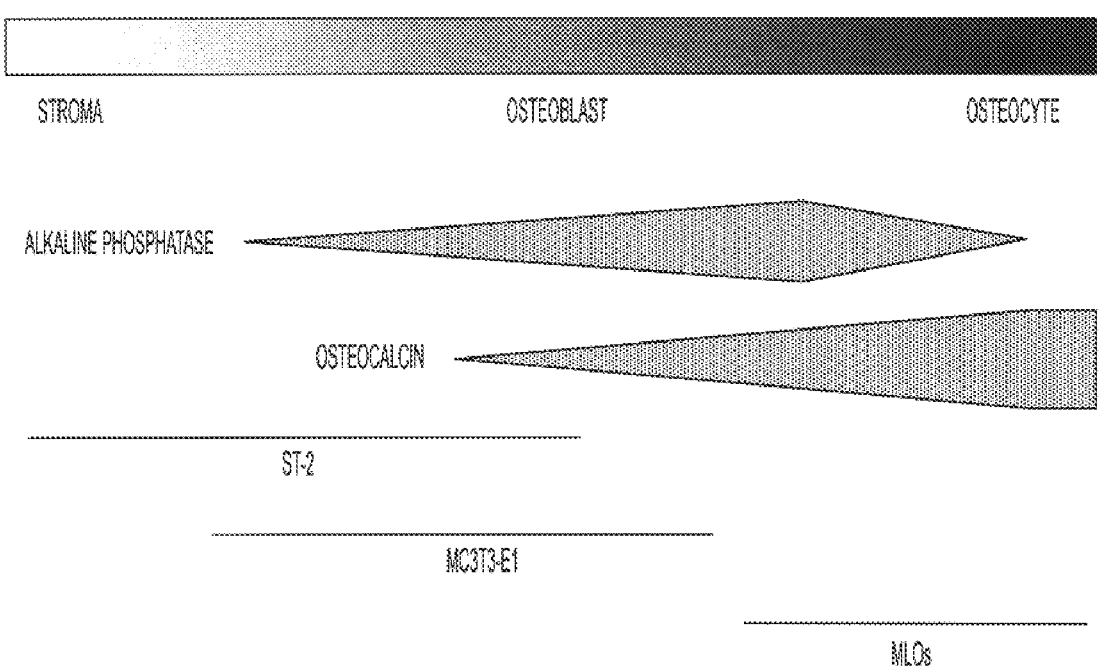
FIG. 13 is a diagram showing the different stages of differentiation of the murine long bone osteocyte cell line.

5.11.1 Quantitation of Alkaline Phosphatase Specific Activity $4\times10^4$ cells were plated on collagen-coated 24 well plates, and cultured with α-MEM+5% FCS+5% CS or α-MEM+10% FCS. Media were changed every 3 days. Cell cultures were stopped after 2, 5, 8, 11, 14, 17 days, and washed 2× with PBS. Cells were lysed by 2 freeze-thaw cycles with 200 µl of 0.05% Triton X-100. 10 µl of lysate was used to measure protein concentration using the micro Bradford method (Bio-Rad Laboratories, Hercules, Calif., U.S.A.) and alkaline phosphatase activity using 1.5 M 2-amino-2-methyl-1-propanol (AMP) buffer (pH 10.3) containing 5 mM P-nitrophenol phosphate substrate according to a previously described method (Bonewald et al., 1991). The MLO-A-F clones express alkaline phosphatase activity which ranged from very low producers to relatively high producers of alkaline phosphatase as compared with osteoblast-like cell lines (FIG. 3). The cultured cell line:MLO-Y have low alkaline phosphatase activity (FIG. 10). MLO-Y4 cells expressed very low alkaline phosphatase specific activity throughout the entire culture period compared with primary osteoblasts and OCT-1 cells cultured in both 10% FBS (FIG. 17B) and 5% CS (data not shown) containing medium.

5.12 Mineralization Study

Figure 5:
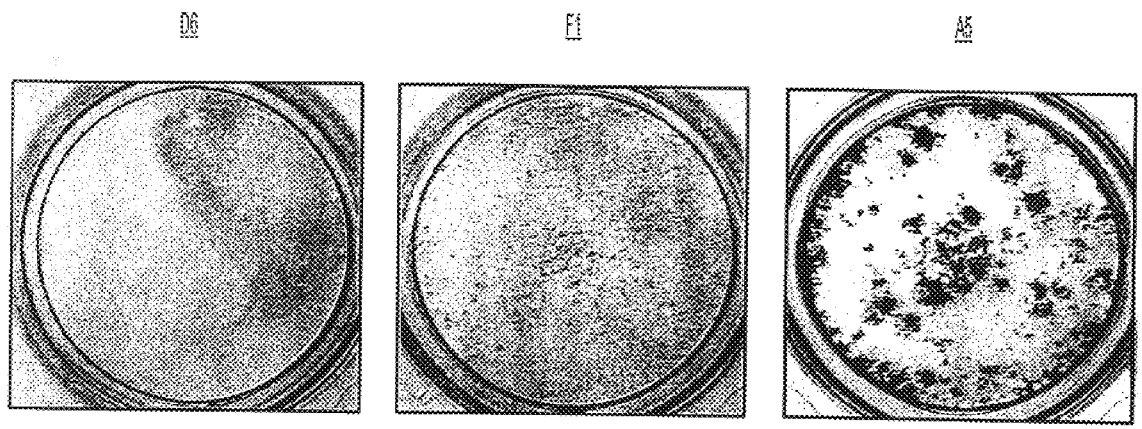
FIG. 5 is an example of the variation of Von Kossa staining for three of the osteocyte cell lines (D6, F1, A5).
Figure 6:
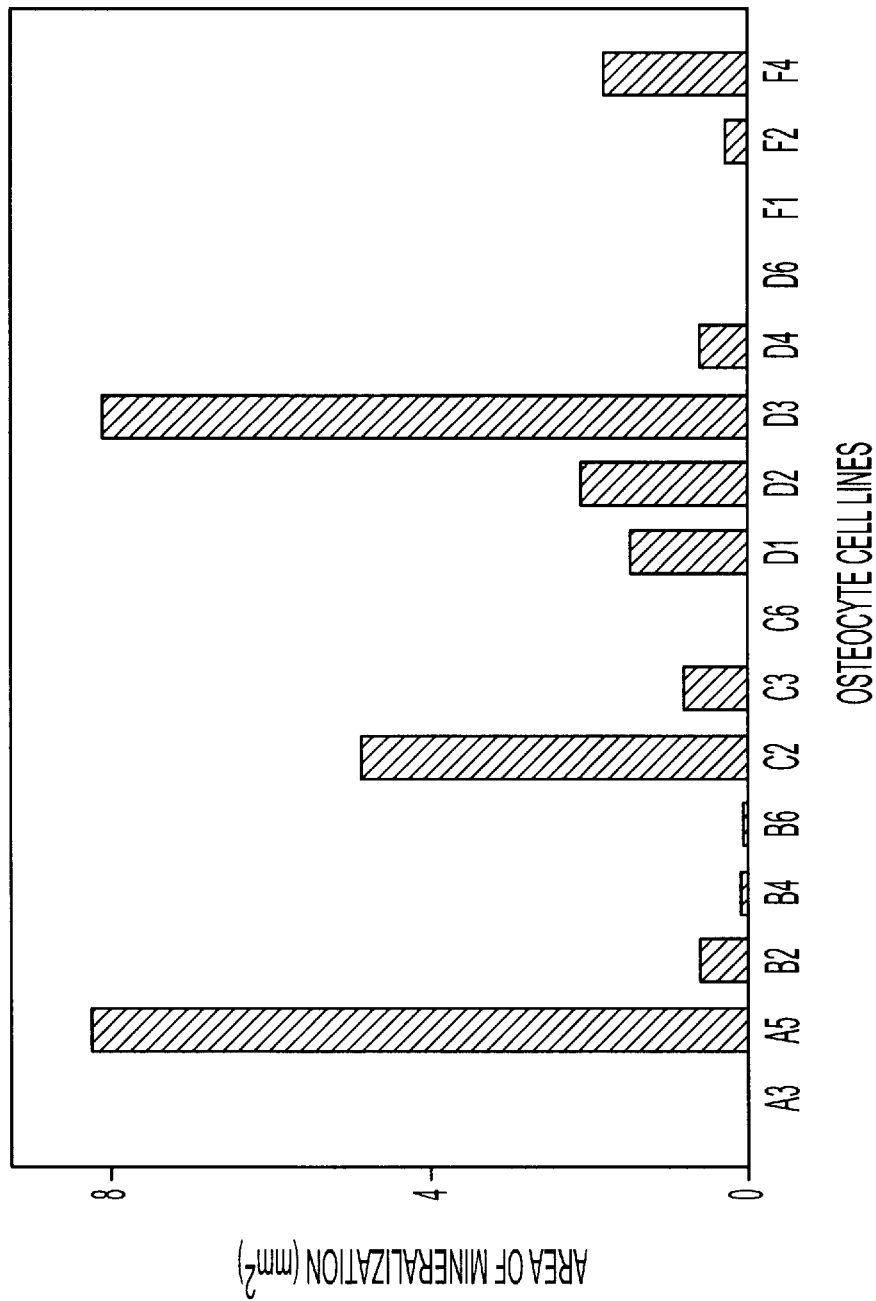
FIG. 6 shows the quantitation of the area of mineralization as determined by Von Kossa staining in various osteocyte cell lines.

The capacity of osteocytes to form mineralized nodules was tested according to a previously described technique (Bharagava et al., 1988). $2\times10^4$ cells were plated on each well of collagen-coated 24 well plates with α-MEM+5% FCS+5% CS with or without 5 mM β-glycero phosphate, 100 µg/ml ascorbic acid and $1\times10^{-8}$ M dexamethasone. The media were changed every 3 days. After 14 days culture plates were washed with PBS and fixed with 10% buffered formalin for 10 min. Fixed plates were stained by the Von Kossa method (Harris et al., 1994). Three of the osteocyte cell lines were found to spontaneously form what appears to be mineralized nodules as determined by Von Kossa staining even in the absence of beta glycerol phosphate (FIGS. 5 and 6).

5.13 Cell Lines Used as Controls

The MC3T3-E1 cells are a murine osteoblast cell line established from normal newborn mouse calvaria (Kodama et al., 1982); the OCT-1 cells are an osteoblast-like cell line established from calvaria of newborn transgenic mice carrying the osteocalcin promoter driving the expression of the large T-antigen (Chen et al., 1995); and the 2T3 and 2T9 are osteoblast-like cells established from calvaria of newborn transgenic mice expressing the bone morphogenetic protein-2 (BMP-2) promoter driving the expression of the large T-antigen (Ghosh-Choudhury et al., 1996, Ghosh-Choudhury et al., submitted). These murine osteoblast-like cell lines were cultured in α-MEM supplemented with either 5% FCS and 5% CS or 10% FCS, and used for comparison to the osteocyte cell lines. Primary osteoblastic cells were isolated from neonatal mouse calvaria by sequential collagenase digestion according to the previously described method of Takahashi and coworkers (Takahashi et al., 1988) with a minor modification, using 2 day old neonatal mice instead of fetal mice. Fractions 3 to 6 were used.

5.14 Characteristics of Cloned Cell Lines

Here we have shown the characteristics of several cloned cell lines which possess properties similar to those described for osteocytes. The clones isolated from Fraction 10, clones D1, D3, D6, C2, A5, and F1 all express T-antigen and osteocalcin and three of the clones express estrogen receptor (C2, A5, F1), while three do not (D1, D3, and D6). The morphology of these 6 cell lines range from the small, stellate or 'star-like' shape (D1, D3, D6) to cells which express very long slender cytoplasmic processes (C2, A5, and F1). These cells also expressed various amounts of alkaline phosphatase from low (1l, D6) to relatively high levels (D3, C2, A5, and F1). These cells may represent various stages of osteocyte differentiation.

Figure 9:
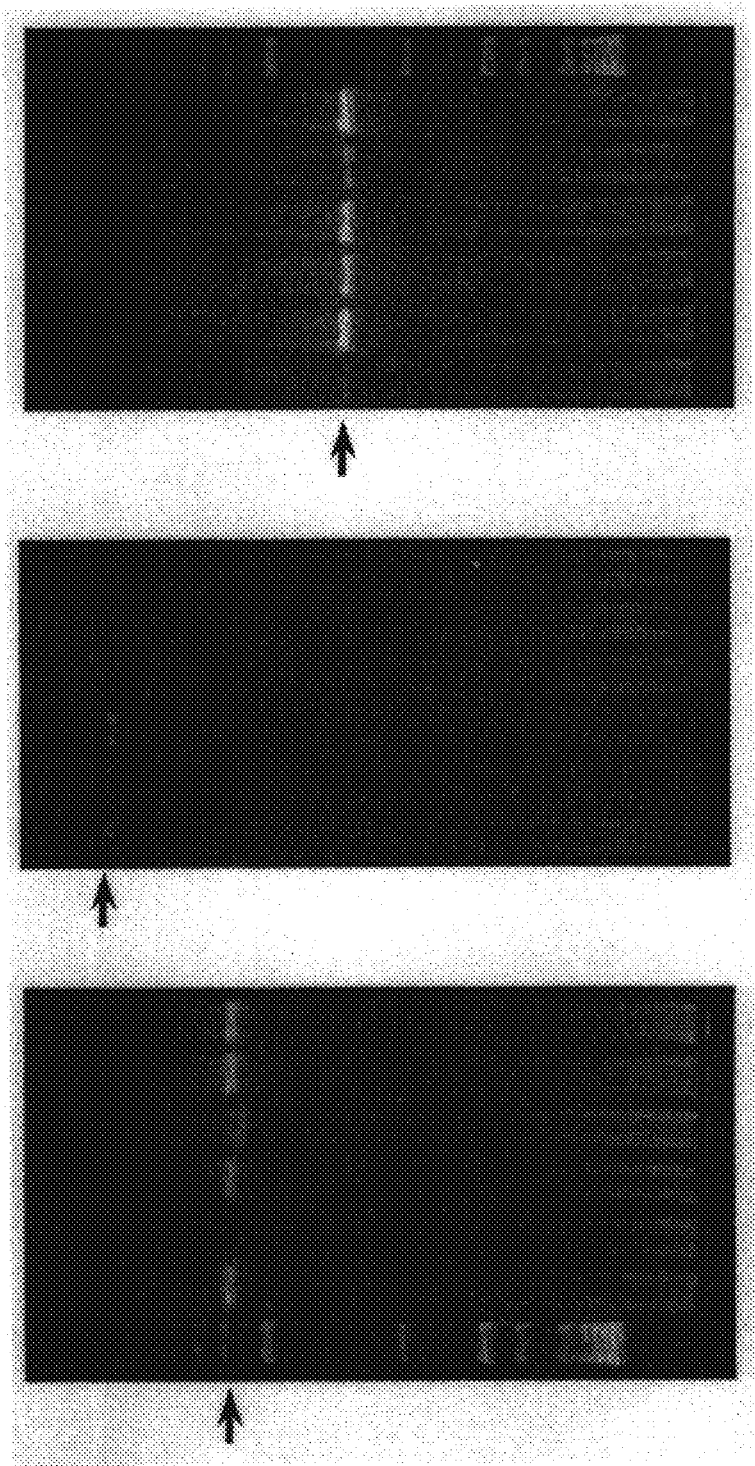
FIG. 9 shows the expression of osteopontin, Type I collagen and lack of expression of OSF-2 by RT-PCR in cultured osteocyte:MLO-Y as compared to other cell types.

In contrast to these cell lines, cultured osteocyte cells:MLO-Y, established from fractions 3–5 possessed numerous dendritic processes. The MLO-Y were positive for T-antigen, osteocalcin (FIG. 8), osteopontin and collagen type 1 but did not express OSF-2 (FIG. 9). MLO-Y cells express low level of alkaline phosphatase compared to primary osteoblasts (FIG. 10). One cell line, MLO-Y4, which derived from MLO-Y also, does not express the osteoblast specific factor-2 (OSF-2), a marker of osteoblasts. This is in contrast to a series of osteoblast cell lines which were analyzed at the same time, which includes primary osteoblasts, OCT-1 osteoblast cell lines, MC3T3-E1 cells, 2T3 and 2T9 cells and ST-2 cells. Therefore, OSF-2 is a negative marker for this cell line and may be a negative marker for osteocytes in vivo.

The cell line was named murine long bone osteocyte-Y4 (MLO-Y4) to emphasize the fact that it was established from long bones, the bones that respond to increased mechanical stress with an increase in bone formation. As the best marker for mammalian osteocytes at the time was their morphology (Mikuni-Takagaki et al., 1995; van der Plas et al., 1992; Nijweide et al., 1988; Palumbo et al., 1990 (ref.31)), this cell line was selected on the basis of expression of dendritic processes, a characteristic morphologic feature of osteocytes.

MLO-Y4 cells express proteins also expressed by osteoblasts such as osteocalcin, osteopontin, connexin 43, CD44, alkaline phosphatase and type I collagen but in relative amounts described for osteocytes. The low expression of alkaline phosphatase and high expression of osteocalcin by MLO-Y4 cells supports the hypothesis that the MLO-Y4 cell line is osteocytes as reports by others show this pattern of expression in primary osteocytes (Mikuni-Takagaki et al., 1995). However, the low expression of type I collagen in MLO-Y4 cells compared to osteoblasts contrasts with a report by Aarden and co-workers (Aarden et al., 1994) but is in agreement with reports by others (Sandberg et al., 1988; Ikeda et al., 1995) and by Nijweide and co-workers who have found that type I collagen is produced in relatively low abundance by osteocytes compared with osteoblasts (personal communication). Our results are also in conflict with the reports by Hughes and co-workers (Hughes et al., 1994) and Nakamura and co-workers (Nakamura et al., 1995) who used immunohistochemical techniques to show that osteocytes are positive for CD44 whereas osteoblast and lining cells are negative. However, Hassan and co-workers (Hassan et al., 1996) have recently shown that osteoblasts at different stages of maturation express mRNA and protein for CD44 both in vivo and in vitro. In the present study, both osteoblast cell lines tested, MC3T3-E1 and OCT-1, primary osteoblasts and MLO-Y4 express CD44. Also recently, a human preosteocytic cell line (HOB-01-C1) has been established and characterized (Bodine et al., 1996). Not only was this preosteocytic cell line positive for CD44, but so were the osteoblastic cell lines used for comparison. These data suggest that CD44 is not a specific marker for osteocytes.

Gap junctions are conduits for cell to cell communication (for review, see Edelson, 1990). Gap junctions penetrate the cell membranes of two communicating cells to allow the flow of low molecular weight signalling molecules such as $Ca^{2+}$, cAMP and inositol triphosphate. Gap junctions are composed of structurally related proteins known as connexins. Several connexins have been shown to be expressed by osteoblasts (Schirrmacher et al., 1992; Schiller et al., 1992; Civitelli et al., 1993; Chiba et al., 1994; Steinberg et al., 1994). By Northern analysis, MC3T3-E1 cells have been shown to express large amounts of connexin 43 mRNA (Chiba et al., 1993) and cultured osteoblasts from newborn rat calvaria also have been shown to express large amounts of this protein (Schirrmacher et al., 1992). As the expression of connexin 43 has recently been described for osteocytes in vivo (Mason et al., 1996), we examined MLO-Y4 cells for expression of this gap junction protein. We are surprised to find very large amounts of connexin 43 protein produced by the MLO-Y4 cells, especially when compared to equivalent amounts of brain tissue (the positive control). Our data suggest that osteocytes may be the major source of connexin 43 in bone, especially when compared to osteoblasts.

Osteoblast-specific factor 2 (OSF-2) was recently cloned from an MC3T3-E1 library and shown to have homology with an insect protein, fasciclin 1 that functions as a homophilic adhesion molecule (Takeshita et al., 1993). OSF-2 was expressed in primary osteoblasts and MC3T3 cells and in lung tissue. Brain, heart, kidney, liver, muscle, placenta, spleen, testis, and thymus were negative for this marker. It is not known if OSF-2 is expressed by osteocytes or other bone cells. The cell line MLO-Y4 does not express OSF-2 mRNA when compared to the osteoblast cell lines OCT-1 and MCT3T3-E1 and primary oesteoblasts analyzed in the same experiments. Therefore, OSF-2, a putative bone adhesion molecule, is a negative marker for this cell line and may be a negative marker for osteocytes in vivo.

Previously, two osteoblastic cell lines were established from the same transgenic mice used in the present study (Chen et al., 1995). These transgenic mice contain a 2.6 kb fragment of the rat osteocalcin promoter driving the expression of SV40 large T-antigen. Previous studies have demonstrated the usefulness of this approach for developing immortalized cell lines (Efrat et al., 1988; Windle et al., 1990). These cell lines termed OCT-1 and OCT-2, were described by their capacity to differentiate into osteoblast-like cells. OCT-1 and OCT-2 were derived from the calvaria of one founder osteocalcin T-antigen transgenic mouse after sequential digestion using trypsin and collagenase. In contrast, in the present experiments, cells were isolated from the long bones of young 14 day old mice through a series of digestions designed to select for cells encapsulated within the mineralized bone matrix. Also, in contrast to the OCT-1 and OCT-2 cells, the osteocyte cell lines appear to produce large amounts of osteocalcin. However, like OCT-1 and OCT-2 cell lines, four of the fraction 10 cell lines (D1, D3, C2, and A5) were observed to form Von Kossa positive nodules after long term culture.

Lanyon and coworkers (Pead et al., 1989; Skerry et al., 1989; Rawlinson et al., 1993) have performed numerous studies examining the effects of mechanical loading on bone in vivo and propose that the osteocyte is the major cell responding to mechanical stress. Sensors and/or transducers on osteocytes appear to respond to load-induced strain. Glucose 6-phosphate dehydrogenase activity increases transiently in osteocytes soon after loading and loading also appears to induce $PGE_2$ and $PGI_2$ production by these cells. Lean and coworkers (1994) have shown that osteocytes respond to mechanical loading with an increase in mRNA for insulin-like growth factor I within 6 hours. Isolated osteocytes, but not osteoblasts nor periosteal fibroblasts react to pulsating fluid flow with a release of prostaglandin $E_2$ (Klein-Nulend et al., 1995). Mikuni-Takagaki and co-workers (1996) concluded from their studies that isolated osteocytes respond differently from young osteocytes and osteoblasts to both low physiological strain and to higher magnitudes of strain. It will be of interest to conduct similar studies using the cell lines isolated in this study to determine if the responses of this cell line are similar to isolated primary oestocytes.

In summary, numerous future studies are planned for these cell lines, including studies to determine what factors are produced upon nochanical loading, and to also examine cell-to-cell communication between the osteocyte cells.

5.15 Production of Monoclonal Antibodies Specific for Osteocytes

Monoclonal antibodies specific for osteocytes were generated using MLO-Y cells described in 5.4 as an immunogen.

5.15.1 Immunization of Rats With MLO-Y Cells

Two-month old LOU rats (from Harlan, Indianapolis, Ind.) were pre-bled before immunization. Each rat was injected subcutaneously with $3.2 \times 10^7$ MLO-Y cells in complete Freund's adjuvant. Three weeks later the animals were bled and boosted intraperitoneally with the same number of cells but in incomplete Freund's adjuvant. This was repeated 2 more times before the final boost with living cells were given subcutaneously and intraperitoneally without adjuvant. The animals were sacrificed and the final bleeding was performed.

5.15.2 Preparation of Hybridoma Producing Osteocyte-Specific Monoclonal Antibody The spleen, a source of antibody-producing cells, of one rat was delivered to the Institutional Hybridoma Facility at the University of Texas Health Science Center directed by Anna Lazzell. Hybridomas were generated according to the procedure of Oi and Herzenberg (1980) with the drop-wise addition of 505 polyethylene-glycol solution into a NS-1/spleen cell mixture. The supernatants from 96-well plates were evaluated 10–14 days later for the presence of antibody.

5.15.3 Screening and Characterization Methods for Monoclonal Antibodies

Preparation of Primary Osteoblasts and Inner Bone Lysate

Calvaria and long bones were removed from six-week old C57bl mice purchased from Harlan (Indianapolis, Ind.). The marrow was flushed from the long bones. The bones were cut into pieces, washed 2× with Hank's solution and then serially digested with collagenase (0.75 mg/ml) for 20 min each at 37° C. to give six digestions. The cells were collected from each digestion and lysed in sample buffer for Sodium Dodecyl Sulphate-PolyAcrylamide Gel Electrophoresis (SDS-PAGE). The remaining bone was further minced and also lysed in sample buffer. The samples were boiled for 5 min before application to SDS-PAGE.

SDS-PAGE and Western Blotting

SDS-PAGE and western blotting were performed essentially as described previously (Bonewald et al., 1991) with the following modifications: The membranes were blocked with 5% skim milk in tris-buffered saline (TBS). The blot was then incubated with undiluted supernatant of the hybridoma clones for 3–4 hours before washing and the addition of horse-radish peroxidase conjugated anti-rat IgG 1:5000 dilution in 1% skim milk/TBS and then developed using an NEN kit as per manufacturers instructions.

Enzyme-linked Immunoassay (ELISA)

The ELISAs were performed essentially as described previously (Bonewald et al., 1992) with the following modifications: The cells were grown in 96 well plates until confluent when they were fixed with 3% paraformaldehyde/2% sucrose. The background was blocked with 1% skim milk for 2 to 4 months in storage at 4° C. Undiluted hybridoma supernatant was added at 70 μl/well for 2 hours; the secondary antibody was horse-radish peroxidase conjugated anti-rat IgG and the plates were developed with the OPD reagent.

Immunohistochemical Staining

The cells were fixed in 96 well plastic plates using 3% paraformaldehyde/2% sucrose but only for the monoclonal antibody clone, 9C11, were the cells then permeabilized with methanol. Staining was performed as described previously (Kato et al., in press) with the following modifications: Blocking solution was 1% skim milk/1% goat serum, the cells incubated with non-diluted hybridoma supernatant for 1.5 hours and the secondary biotinylated goat anti-rat IgG antibody at room temperature for 30 min. The ABC complex was added according to manufaturer's instructions for 30 min and the peroxidase substrate reaction proceeded for 2–10 min before stopping by washing.

5.15.4 Isolation and Characterization of Monoclonal Antibodies Specific for Osteocytes Initially two rats were immunized with the MLO-Y cells. Immune sera from one of the rats was tested against a series of tissues and sources of murine osteoblasts and osteocytes and compared to the murine osteoblast cell line MC3T3-E1 cells. As can be seen, a band of approximately 40 kDa is present in the MLO-Y4 cells which is also highly expressed in cells isolated from the osteocyte preparation of murine long bone (see FIG. 1). A faint band is also present in any of the other tissues, the osteoblast preparations or MC3T3 cells. Unfortunately, monoclonals were not generated from this rat due to loss of this animal.

Of the next six rats which were immunized with MLO-Y cells, the animal whose serum showed the greater number of bands specific for the MLO-Y4 cells compared to MC3T3 and OCT-1 cells, was chosen for monoclonal antibody production. As can be seen in FIG. 2, at least 5 bands appear to be present in the MLO-Y4 lysate which are not present in the MC3T3 or OCT-1 lysates.

The pooled fusion clones were screened using ELISAs of fixed MC3T3 cells and fixed MLO-Y4 cells and by western blots of MLO-Y4 lysates. One clone, 9C11, reacted with a 40 kDa band in MLO-Y4 cell lysates by western blotting. This clone was then tested against MC3T3 and OCT-1 lysates as shown in FIG. 3. As can be seen this antibody was highly specific for MLO-Y cells.

Figure 4:
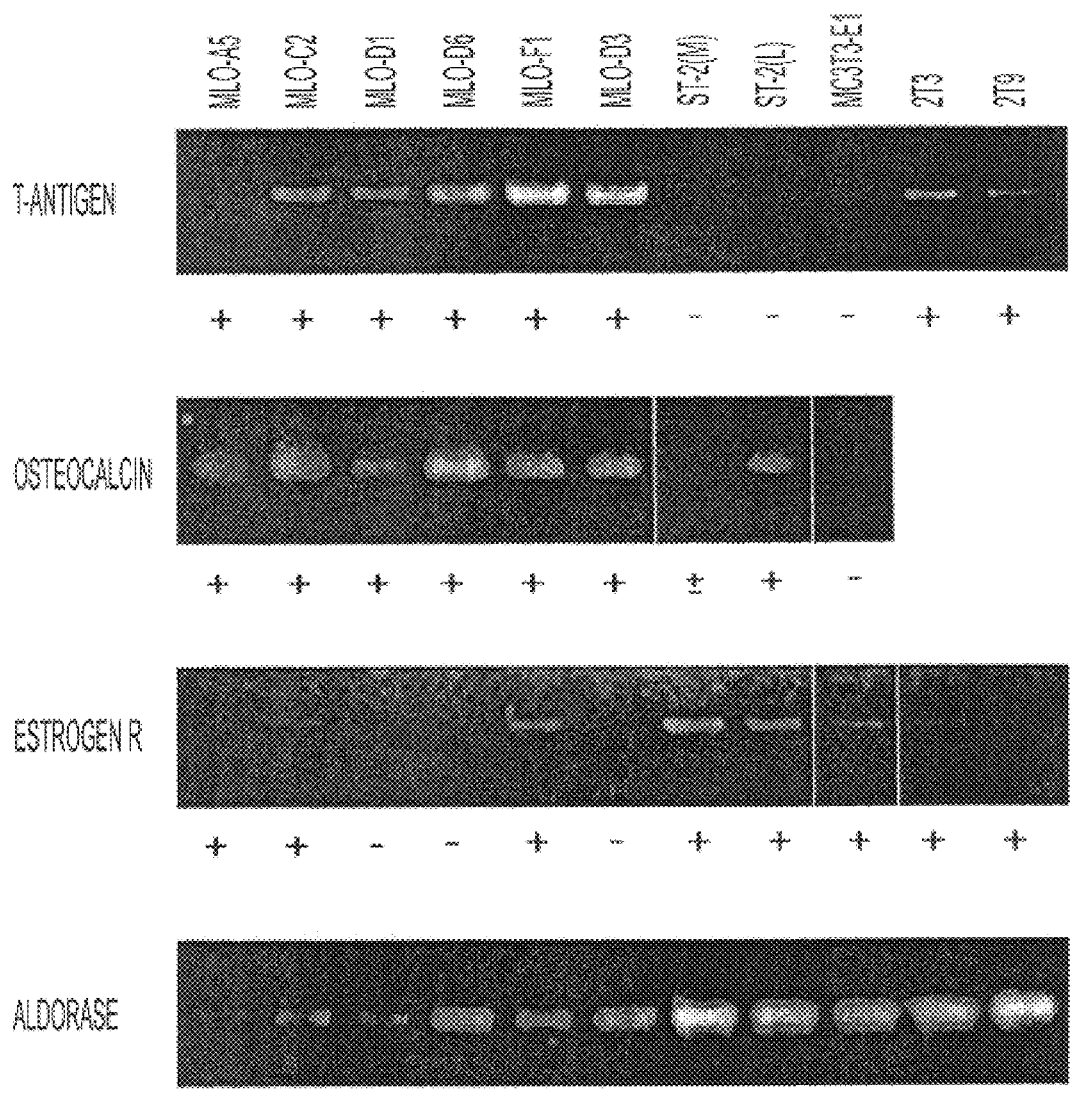
FIG. 4 shows the expression of T-antigen, osteocalcin, and estrogen receptor by RT-PCR in the osteocyte cell lines as shown in FIG. 3 and compared to osteoblast like cell lines.

The clone 9C11 was then tested against a series of cell and bone lysates from mouse long bone and mouse calvaria. No reactivity was observed with cell lysates from digestions 1 through 7, but the lysate of the remaining bone pieces revealed a band at 40 kDa for the long bone (LB F8) and a band at approximately 100 kDa for the calvarial pieces (Cal F8) as shown in FIG. 4. The amount of total protein loaded can be seen in FIG. 4B showing that almost undetectable amounts of protein were loaded for LB F8, yet reactivity was observed by Western blotting. Even though a broad band is observed with the Ponceau S staining of the sample Cal F8, the western blot showed a smaller, more discreet band than the broad protein band. These observations have been repeated three times.

Figure 1:
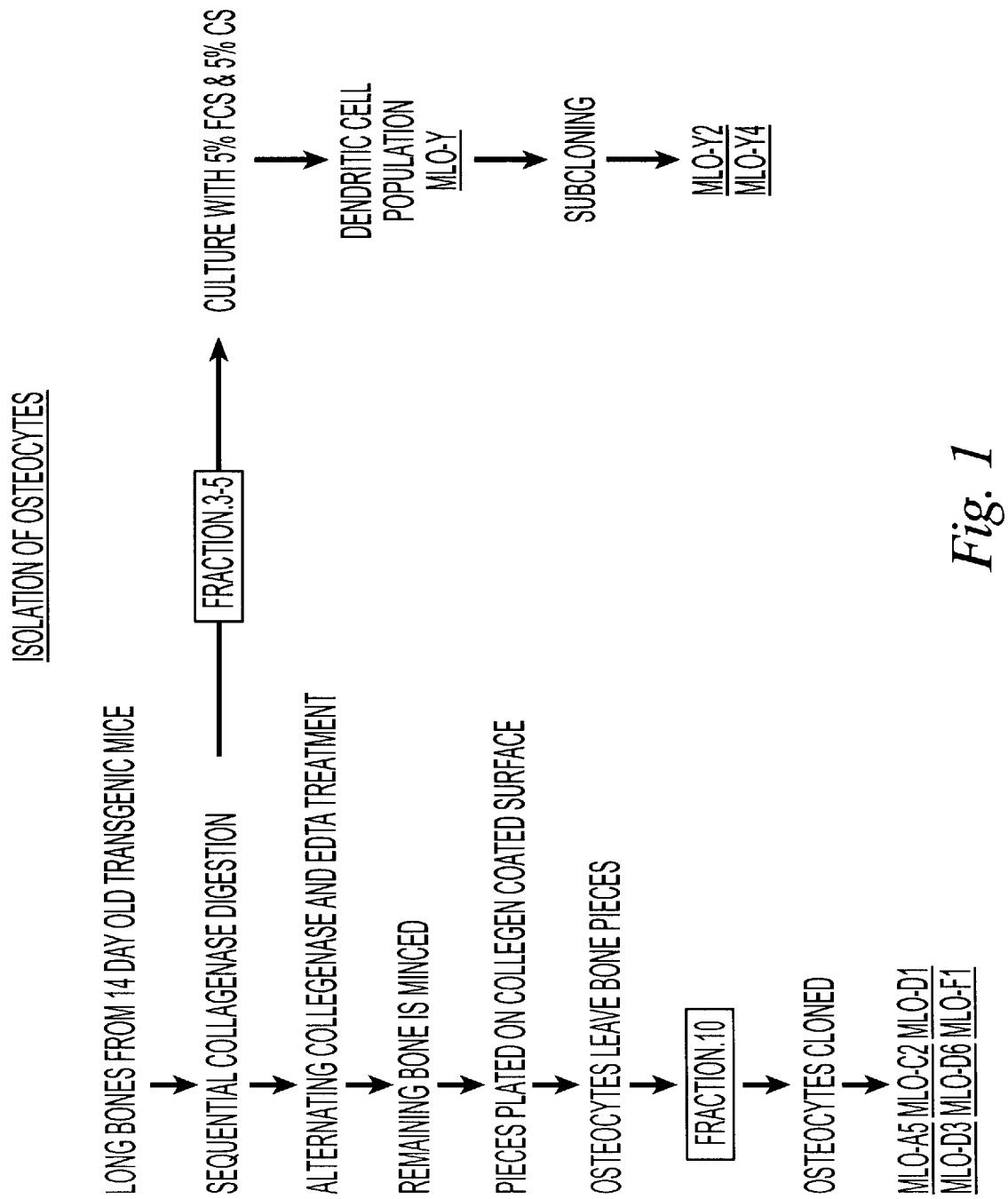

Although the rat immune serum as shown in FIG. 1 also appears to recognize an osteocyte-specific band of approximately 40 kDa, it is not clear at this time if this band is identical to the 40-kDa band recognized by 9C11.

The 40 kDa band as detected by clone 9C11 can be induced in murine calvarial osteoblasts and OCT-1 cells with treatment with recombinant BMP-2 as shown in FIG. 5. OCT-1 cells and murine calvarial osteoblasts differentiate in culture to form bone-like nodules which mineralize in the presence of ascorbic acid and beta-glycerolphosphate (Chen et al., 1995). As can be seen in FIG. 5, the antigen detected by 9C11 antibody is expressed by these cells after four weeks of culture. These observations suggest that the osteoblasts and osteoblast cell line differentiate in culture to become osteocytes after the period of nodule formation but during mineralization of the nodules.

Immunohistochemistry was performed on fixed MLO-Y4 cells using media alone and clone 9C11. As can be seen in FIG. 6, small, round, intracytoplasmic organelles were stained in the MLO-Y4 cells. The nature of these organelles at this time is not known.

Three clones were chosen which reacted strongly and selectively with MLO-Y4 cells when compared to MC3T3 cells by ELISA. The results are shown in FIG. 7. These clones were then tested for their immunoreactivity to fixed MC3T3, OCT-1, and MLO-Y4 cells by immunohistochemistry. As can be seen in FIG. 8, clones 9D9 (produced by hybridoma 9D9-2F5) and 11H4 (produced by hybridoma 11H4-1C7) only stained MLO-Y4 cells and not MC3T3 nor OCT-1 cells. The pattern of staining for 9D9 was nuclear and the pattern for 11H4 was cytoplasmic. As shown in FIG. 9, clone 9A3 (produced by hybridoma 9A3-2G8) stained both OCT-1 and MLO-Y4 cells but was negative for MC3T3 cells. These three clones do not recognize any bands by western blot analysis (data not shown).

As described above, here we show the production of four hybridomas which appear to be specific for osteocytes. At the present time, the antigens or epitopes for these antibodies have not been characterized or identified. These antigens may be important in the functioning of osteocytes whether in sensing mechanical stress, in cell-cell communication, or other osteocyte specific functions. All four hybridomas appear to be recognizing different antigens. The 9C11 hybridoma recognizes bands on gels as detected by western blotting whereas the other three clones only appear to recognize antigens on the cell and not bands in cell lysates. The clone 9C11 also recognizes small intracellular vesicles. This antigen appears to be osteocyte specific as osteoblasts and osteoblast-like cells which undergo differentiation in culture to produce bone nodules begin to express this antigen after mineralization. The nature of this antigen or the mechanisms by which it functions in the osteocyte remains to be determined.

The subject invention is not intended to be limited in scope to the hybridomas deposited, but they are intended as a single illustration of hybridomas that produce osteocyte-specific monoclonal antibodies, as defined herein. Any hybridoma that is functionally equivalent is within the scope of the subject invention. By the term "functionally equivalent," it is meant that an antibody is capable of competing with the 9C11, 9A3, 9D9, or 11H4 monoclonal antibody in binding to the epitope of an osteocyte. The term also includes osteocyte-specific monoclonal antibodies, as defined herein, that bind to an epitope different from that which each of these four monoclonal antibodies binds.

6. DEPOSIT

Samples of the cell line MLO-Y4 were deposited with the ATCC, 10801 University Blvd., Manassas, Va. 20110-2209 in accordance with the Budapest Treaty on the Deposit of Microorganisms on Jul. 31, 1996, and accorded accession No. CRL-12161.

Samples of the hybridomas, 9A3-2G8, 9D9-2F5, and 11H4-1C7 were also deposited with ATCC on Sep. 3, 1997, and their accession Nos. are ATCC HB-12395, HB-12396, and HB-12397, respectively.

The hybridoma which produced 9C11 was unfortunately lost and, therefore, could not be deposited.

What is claimed is:

1. A method for the production of an osteocyte cell line, said cell line having the following properties: available to passage more than 20 times, a stellate shape with dendritic processes and expresses increased levels of osteocalcin compared to mouse osteoblast or osteoblast-like cell lines, and said method comprising the steps of:
    (a) isolating bones from a transgenic mouse whose genome contains an osteocalcin promoter driven T-antigen transgene and preparing bone pieces from the bones;
    (b) digesting the bone pieces with collagenase solution and harvesting cells into fetal and adult calf serum supplemented medium; and
    (c) plating the harvested cells and isolating said cell line by selecting a single colony.

2. The method of claim 1, wherein said bone is selected from the group consisting of tibiae, femurs and humeri.

3. The method of claim 1, wherein said medium is alpha-MEM and the supplement is 5% fetal calf serum and 5% adult calf serum.

4. The method of claim 1, wherein said cell line is a mature osteocyte cell line.

5. The method of claim 1, wherein said cell line is a preosteocyte cell line.

6. An immortalized osteocyte cell line which is prepared by the method according to claim 1.

7. A method for the production of an osteocyte cell line, said cell line having the following properties: available to passage more than 20 times, a stellate shape with dendritic processes and expresses increased levels of osteocalcin compared to mouse osteoblast or osteoblast-like cell lines, and said method comprising the steps of:
    (a) isolating bones from a transgenic mouse whose genome contains an osteocalcin promoter driven T-antigen transgene and preparing bone pieces from the bones;
    (b) digesting the bone pieces with collagenase solution and harvesting remaining bone pieces;
    (c) alternately treating the remaining bone pieces with EDTA and collagenase and harvesting remaining bone pieces;
    (d) mincing the remaining bone pieces after EDTA and collagenase treatment into smaller chips;
    (e) culturing the bone chips for a period sufficient to allow migration of cells from the bone chips;
    (f) harvesting and culturing the migrated cells with fetal and adult calf serum supplemented medium; and
    (g) isolating said cell line by selecting a single colony.

8. The method of claim 7, wherein said bone is selected from the group consisting of tibiae, femurs and humeri.

9. The method of claim 7, wherein said medium is alpha-MEM and the supplement is 5% fetal calf serum and 5% adult calf serum.

10. The method of claim 7, wherein said cell line is a mature osteocyte cell line.

11. The method of claim 7, wherein said cell line is a preosteocyte cell line.

12. An immortalized osteocyte cell line which is prepared by the method according to claim 7.

13. A method for the production of a cultured osteocyte cell, said cultured osteocyte cell having the following properties: available to passage more than 20 times, a stellate shape with dendritic processes and expresses increased levels of osteocalcin compared to mouse osteoblast or osteoblast-like cell lines, and said method comprising the steps of:
    (a) isolating bones from a transgenic mouse whose genome contains an osteocalcin promoter driven T-antigen transgene and preparing bone pieces from the bones;
    (b) digesting the bone pieces with collagenase solution and harvesting cells; and
    (c) culturing the harvested cells with fetal and adult calf serum supplemented medium.

14. The method of claim 13, wherein said bone is selected from the group consisting of tibiae, femurs and humeri.

15. The method of claim 13, wherein said medium is alpha-MEM and the supplement is 5% fetal calf serum and 5% adult calf serum.

16. An immortalized osteocyte cell prepared by the method according to claim 13.

17. A method of screening for an osteocyte differentiation modification factor comprising:
    placing an immortalized osteocyte cell in the presence of a factor to be tested, wherein said osteocyte cell is prepared by the method according to claim 13;
    measuring a level of a product or activity correlatable with differentiation of the osteocyte expressed by the osteocyte cell in the presence of the factor; and
    comparing the levels of the expression of the product or activity in the presence and the absence of the factor, wherein a difference in the level of the product or activity in the presence of the factor indicates that the factor is an osteocyte differentiation modification factor.

18. A method of screening for an osteocyte binding factor comprising:

placing an immortalized osteocyte cell in the presence of a factor to be tested; and measuring a level of the factor which is bound to the osteocyte cell so as to determine whether the factor is an osteocyte binding factor, wherein said osteocyte cell is prepared by the method according to claim 13.

19. A method for the production of a cultured osteocyte cell, said cultured osteocyte cell having the following properties: available to passage more than 20 times, a stellate shape with dendritic processes and expresses increased levels of osteocalcin compared to mouse osteoblast or osteoblast-like cell lines, and said method comprising the steps of:

(a) isolating bones from a transgenic mouse whose genome contains an osteocalcin promoter driven T-antigen transgene and preparing bone pieces from the bones;

(b) digesting the bone pieces with collagenase solution and harvesting remaining bone pieces;

(c) alternately treating the remaining bone pieces with EDTA and collagenase and harvesting remaining bone pieces;

(d) mincing the remaining bone pieces after EDTA and collagenase treatment into smaller chips;

(e) culturing the bone chips for a period sufficient to allow migration of cells from bone chips; and (f) harvesting and culturing the migrated cells with fetal and adult calf serum supplemented medium.

20. The method of claim 19, wherein said bone is selected from the group consisting of tibiae, femurs and humeri.

21. The method of claim 19, wherein said medium is alpha-MEM and the supplement is 5% fetal calf serum and 5% adult calf serum.

22. An immortalized osteocyte cell prepared by the method according to claim 19.

23. A method of screening for an osteocyte differentiation modification factor comprising:

placing an immortalized osteocyte cell in the presence of a factor to be tested, wherein said osteocyte cell is prepared by the method according to claim 19;

measuring a level of a product or activity correlatable with differentiation of the osteocyte expressed by the osteocyte cell in the presence of the factor; and comparing the levels of the expression of the product or activity in the presence and the absence of the factor, wherein a difference in the level of the product or activity in the presence of the factor indicates that the factor is an osteocyte differentiation modification factor.

24. A method of screening for an osteocyte binding factor comprising:

placing an immortalized osteocyte cell in the presence of a factor to be tested; and measuring a level of the factor which is bound to the osteocyte cell so as to determine whether the factor is an osteocyte binding factor, wherein said osteocyte cell is prepared by the method according to claim 19.

25. An immortalized mouse osteocyte cell line, said cell line being obtained from a transgenic mouse whose genome contains an osteocalcin promoter driven T-antigen transgene, wherein said cell line has the following properties: available to passage more than 20 times, a stellate shape with dendritic processes and increased levels of osteocalcin expression compared to mouse osteoblast or osteoblast-like cell lines.

26. The immortalized cell line of claim 25, wherein said cell line overexpresses T-antigen protein.

27. An immortalized mouse osteocyte cell or a cell obtained by passaging said mouse osteocyte cell having the following properties: available to passage more than 20 times, a stellate shape with dendritic processes and increased levels of osteocalcin expression compared to mouse osteoblast or osteoblast-like cell lines, wherein said osteocyte cell is obtained from a transgenic mouse whose genome contains an osteocalcin promoter driven T-antigen transgene.

28. The immortalized osteocyte cell of claim 27, wherein said osteocyte cell overexpresses T-antigen protein.

29. A method of screening for an osteocyte differentiation modification factor comprising:

placing an osteocyte cell of claim 27 in the presence of a factor to be tested;

measuring a level of a product or activity correlatable with differentiation of the osteocyte expressed by the osteocyte cell in the presence of the factor; and comparing the levels of the expression of the product or activity in the presence and the absence of the factor, wherein a difference in the level of the product or activity in the presence of the factor indicates that the factor is an osteocyte differentiation modification factor.

30. The method of screening for an osteocyte modification factor according to claim 29, wherein said osteocyte cell overexpresses T-antigen protein.

31. A method of screening for an osteocyte binding factor comprising:

placing an osteocyte cell of claim 27 in the presence of a factor to be tested; and measuring a level of the factor which is bound to the osteocyte cell so as to determine whether the factor is an osteocyte binding factor.

32. The method of screening for an osteocyte binding factor according to claim 31, wherein said osteocyte cell overexpresses T-antigen protein.

33. An osteocyte cell line, MLO-Y4 (ATCC accession No. CRL-12161) or a passaged cell line thereof.

* * * * *